(12) United States Patent
Hinman

(10) Patent No.: US 8,562,640 B2
(45) Date of Patent: Oct. 22, 2013

(54) TOOL WITH MULTI-STATE RATCHETED END EFFECTOR

(75) Inventor: Cameron D. Hinman, Thurmond, NC (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1375 days.

(21) Appl. No.: 11/787,605

(22) Filed: Apr. 16, 2007

(65) Prior Publication Data

US 2008/0255588 A1 Oct. 16, 2008

(51) Int. Cl.
*A61B 17/00* (2006.01)

(52) U.S. Cl.
USPC .............................................. 606/205; 606/1

(58) Field of Classification Search
USPC .................................. 606/205–208
See application file for complete search history.

(56) References Cited

U.S. PATENT DOCUMENTS

| | | | |
|---|---|---|---|
| 1,820,463 A | 8/1931 | Klein | |
| 3,060,972 A | 10/1962 | Sheldon | |
| 3,071,161 A | 1/1963 | Ulrich | |
| 3,190,286 A | 6/1965 | Stokes | |
| 3,557,780 A | 1/1971 | Sato | |
| 3,605,725 A | 9/1971 | Bentov | |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A | 12/1988 | Allred et al. | |
| 4,834,761 A | 5/1989 | Walters | |
| 4,854,626 A | 8/1989 | Duke | |
| 4,880,015 A | 11/1989 | Nierman | |
| 4,984,951 A | 1/1991 | Jameson | |
| 5,174,276 A | 12/1992 | Crockard | |
| 5,257,618 A | 11/1993 | Kondo | |

(Continued)

FOREIGN PATENT DOCUMENTS

| | | |
|---|---|---|
| EP | 0 165 718 | 12/1985 |
| EP | 0 598 618 A2 | 5/1994 |

(Continued)

OTHER PUBLICATIONS

Danitz et al.; U.S. Appl. No. 12/109,333 entitled "Articulating instrument," filed Apr. 24, 2008.

(Continued)

*Primary Examiner* — Gary Jackson
*Assistant Examiner* — Amy Shipley

(57) ABSTRACT

The invention provides surgical or diagnostic tools and associated methods that offer improved user control for operating remotely within regions of the body. These tools include a proximally-located actuator for the operation of a distal end effector, as well as proximally-located actuators for articulational and rotational movements of the end effector. Control mechanisms and methods refine operator control of end effector actuation and of these articulational and rotational movements. A multi-state ratchet for end effector actuation provides enablement-disablement options with tactile feedback. The tool may also include other features. A force limiter mechanism protects the end effector and manipulated objects from the harm of potentially excessive force applied by the operator. An articulation lock allows the fixing and releasing of both neutral and articulated configurations of the tool and of consequent placement of the end effector. A rotation lock provides for enablement and disablement of rotatability of the end effector.

28 Claims, 18 Drawing Sheets

(56) References Cited

U.S. PATENT DOCUMENTS

| | | | |
|---|---|---|---|
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,322,064 A | 6/1994 | Lundquist | |
| 5,325,845 A | 7/1994 | Adair | |
| 5,330,502 A | 7/1994 | Hassler et al. | |
| 5,354,162 A | 10/1994 | Burdea et al. | |
| 5,381,782 A | 1/1995 | DeLaRama et al. | |
| 5,403,342 A | 4/1995 | Tovey et al. | |
| 5,405,344 A | 4/1995 | Williamson et al. | |
| 5,425,743 A | 6/1995 | Nicholas | |
| 5,441,494 A | 8/1995 | Ortiz | |
| 5,454,827 A | 10/1995 | Aust et al. | |
| 5,476,479 A | 12/1995 | Green et al. | |
| 5,483,952 A * | 1/1996 | Aranyi | 600/131 |
| 5,486,154 A | 1/1996 | Kelleher | |
| 5,490,819 A | 2/1996 | Nicholas et al. | |
| 5,498,256 A | 3/1996 | Furnish | |
| 5,513,827 A | 5/1996 | Michelson | |
| 5,520,678 A | 5/1996 | Heckele et al. | |
| 5,522,788 A | 6/1996 | Kuzmak | |
| 5,549,636 A | 8/1996 | Li | |
| 5,562,699 A | 10/1996 | Heimberger et al. | |
| 5,570,919 A | 11/1996 | Eusebe | |
| 5,599,151 A | 2/1997 | Daum et al. | |
| 5,609,601 A | 3/1997 | Kolesa et al. | |
| 5,620,415 A | 4/1997 | Lucey et al. | |
| 5,624,398 A | 4/1997 | Smith et al. | |
| 5,626,608 A * | 5/1997 | Cuny et al. | 606/205 |
| 5,632,432 A | 5/1997 | Schulze et al. | |
| 5,643,294 A | 7/1997 | Tovey et al. | |
| 5,647,743 A | 7/1997 | Schmitt | |
| 5,702,408 A | 12/1997 | Wales et al. | |
| 5,704,534 A | 1/1998 | Huitema et al. | |
| 5,713,505 A | 2/1998 | Huitema | |
| 5,716,352 A | 2/1998 | Viola et al. | |
| 5,735,874 A * | 4/1998 | Measamer et al. | 606/208 |
| 5,759,151 A | 6/1998 | Sturges | |
| 5,792,164 A | 8/1998 | Lakatos et al. | |
| 5,807,376 A | 9/1998 | Viola et al. | |
| 5,813,813 A | 9/1998 | Daum et al. | |
| 5,823,066 A | 10/1998 | Huitema et al. | |
| 5,827,323 A | 10/1998 | Klieman et al. | |
| 5,836,960 A | 11/1998 | Kolesa et al. | |
| 5,845,540 A | 12/1998 | Rosheim | |
| 5,846,183 A | 12/1998 | Chilcoat | |
| 5,873,817 A | 2/1999 | Kokish et al. | |
| 5,899,425 A | 5/1999 | Corey et al. | |
| 5,916,146 A | 6/1999 | Allotta et al. | |
| 5,916,147 A | 6/1999 | Boury et al. | |
| 5,921,956 A | 7/1999 | Grinberg et al. | |
| 5,938,678 A | 8/1999 | Zirps et al. | |
| 5,947,984 A | 9/1999 | Whipple | |
| 5,961,532 A | 10/1999 | Finley et al. | |
| 6,019,722 A | 2/2000 | Spence et al. | |
| 6,050,996 A | 4/2000 | Schmaltz et al. | |
| 6,089,412 A * | 7/2000 | Snell et al. | 222/309 |
| 6,117,158 A * | 9/2000 | Measamer et al. | 606/208 |
| 6,161,543 A | 12/2000 | Cox et al. | |
| 6,250,532 B1 | 6/2001 | Green et al. | |
| 6,270,453 B1 | 8/2001 | Sakai | |
| 6,446,850 B2 | 9/2002 | Ming-Shun | |
| 6,464,704 B2 | 10/2002 | Schmaltz et al. | |
| 6,471,641 B2 | 10/2002 | Sakamoto | |
| 6,471,696 B1 | 10/2002 | Berube et al. | |
| 6,482,149 B1 | 11/2002 | Torii | |
| 6,491,626 B1 | 12/2002 | Stone et al. | |
| 6,571,042 B1 | 5/2003 | Kordahi | |
| 6,626,824 B2 | 9/2003 | Ruegg et al. | |
| 6,635,071 B2 | 10/2003 | Boche et al. | |
| 6,638,213 B2 | 10/2003 | Ogura et al. | |
| 6,638,287 B2 | 10/2003 | Danitz et al. | |
| RE38,335 E | 11/2003 | Aust et al. | |
| 6,641,528 B2 | 11/2003 | Torii | |
| 6,644,532 B2 | 11/2003 | Green et al. | |
| 6,666,854 B1 | 12/2003 | Lange | |
| 6,669,254 B2 | 12/2003 | Thom et al. | |
| 6,676,676 B2 | 1/2004 | Danitz et al. | |
| 6,682,541 B1 | 1/2004 | Gifford et al. | |
| 6,743,239 B1 | 6/2004 | Kuehn et al. | |
| 6,746,443 B1 | 6/2004 | Morley et al. | |
| 6,749,560 B1 | 6/2004 | Konstorum et al. | |
| 6,752,823 B2 | 6/2004 | Prestel | |
| 6,764,445 B2 | 7/2004 | Ramans et al. | |
| 6,773,327 B1 | 8/2004 | Felice et al. | |
| 6,817,972 B2 | 11/2004 | Snow | |
| 6,824,548 B2 | 11/2004 | Smith et al. | |
| 6,843,794 B2 | 1/2005 | Sixto, Jr. et al. | |
| 6,858,005 B2 | 2/2005 | Ohline et al. | |
| 6,902,560 B1 | 6/2005 | Morley et al. | |
| 6,942,613 B2 | 9/2005 | Ewers et al. | |
| 6,945,979 B2 | 9/2005 | Kortenbach et al. | |
| 6,960,162 B2 | 11/2005 | Saadat et al. | |
| 6,960,163 B2 | 11/2005 | Ewers et al. | |
| 6,976,969 B2 | 12/2005 | Messerly | |
| 6,994,700 B2 | 2/2006 | Elkins et al. | |
| 7,138,976 B1 | 11/2006 | Bouzit et al. | |
| 7,480,600 B2 | 1/2009 | Massie et al. | |
| 7,553,275 B2 | 6/2009 | Padget et al. | |
| 2001/0023313 A1 | 9/2001 | Ide | |
| 2002/0096177 A1 | 7/2002 | Toti et al. | |
| 2002/0111604 A1 | 8/2002 | Doyle et al. | |
| 2002/0156497 A1 | 10/2002 | Nagase et al. | |
| 2002/0161281 A1 | 10/2002 | Jaffe et al. | |
| 2002/0177750 A1 | 11/2002 | Pilvisto | |
| 2003/0036748 A1 | 2/2003 | Cooper et al. | |
| 2003/0050649 A1 | 3/2003 | Brock et al. | |
| 2003/0078644 A1 | 4/2003 | Phan | |
| 2003/0109898 A1 | 6/2003 | Schwarz et al. | |
| 2003/0114838 A1 | 6/2003 | O'Neill et al. | |
| 2003/0135204 A1 | 7/2003 | Lee et al. | |
| 2003/0149338 A1 | 8/2003 | Francois et al. | |
| 2003/0153902 A1 | 8/2003 | Doyle et al. | |
| 2003/0229271 A1 | 12/2003 | Briscoe et al. | |
| 2003/0233026 A1 | 12/2003 | Saadat et al. | |
| 2004/0054322 A1 | 3/2004 | Vargas | |
| 2004/0138529 A1 | 7/2004 | Wiltshire et al. | |
| 2004/0138700 A1 | 7/2004 | Cooper et al. | |
| 2004/0236316 A1 | 11/2004 | Danitz et al. | |
| 2005/0090809 A1 | 4/2005 | Cooper et al. | |
| 2005/0096694 A1 | 5/2005 | Lee | |
| 2005/0107667 A1 | 5/2005 | Danitz et al. | |
| 2005/0119527 A1 | 6/2005 | Banik et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0009759 A1 | 1/2006 | Chrisitian et al. | |
| 2006/0020287 A1 | 1/2006 | Lee et al. | |
| 2006/0036255 A1 | 2/2006 | Pond et al. | |
| 2006/0058582 A1 | 3/2006 | Maahs et al. | |
| 2006/0094931 A1 | 5/2006 | Danitz et al. | |
| 2006/0111209 A1 | 5/2006 | Hinman et al. | |
| 2006/0111210 A1 | 5/2006 | Hinman | |
| 2006/0111615 A1 | 5/2006 | Danitz et al. | |
| 2006/0111616 A1 | 5/2006 | Danitz | |
| 2006/0199999 A1 | 9/2006 | Ideda et al. | |
| 2006/0201130 A1 | 9/2006 | Danitz | |
| 2007/0276430 A1 | 11/2007 | Lee et al. | |
| 2008/0065116 A1 | 3/2008 | Lee et al. | |
| 2008/0188869 A1 | 8/2008 | Weitzner et al. | |
| 2008/0188871 A1 | 8/2008 | Smith et al. | |

FOREIGN PATENT DOCUMENTS

| | | |
|---|---|---|
| EP | 0 836 833 A2 | 4/1998 |
| EP | 1 132 041 | 9/2001 |
| EP | 1 395 398 B1 | 3/2004 |
| JP | H06-262549 | 9/1994 |
| JP | 01-299768 | 10/2001 |
| WO | WO 01/10292 A1 | 2/2001 |
| WO | WO 02/13682 A1 | 2/2002 |
| WO | WO 2004/019769 A1 | 3/2004 |

(56) References Cited

FOREIGN PATENT DOCUMENTS

| WO | WO 2004/105578 A3 | 12/2004 |
| WO | WO 2005/067785 A1 | 7/2005 |
| WO | WO 2005/120326 A3 | 12/2005 |
| WO | WO 2005/120327 A3 | 12/2005 |
| WO | WO 2006/057699 A1 | 6/2006 |
| WO | WO 2006/057700 A1 | 6/2006 |
| WO | WO 2006/057702 A2 | 6/2006 |
| WO | WO 2006/073581 A1 | 7/2006 |

OTHER PUBLICATIONS

Isbell Jr., Lewis; U.S. Appl. No. 12/542,589 entitled "Instrument with articulation lock," filed Aug. 17, 2009.

Hinman, Cameron; U.S. Appl. No. 12/508,478 entitled "Articulating mechanism," filed Jul. 23, 2009.

Danitz et al.; U.S. Appl. No. 12/766,818 entitled "Articulating instruments with joystick control," filed Apr. 23, 2010.

Danitz, David J.; U.S. Appl. No. 12/766,820 entitled "Articulating mechanism with bifurcating control," filed Apr. 23, 2010.

Danitz, David J.; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Hinman et al.; U.S. Appl. No. 12/816,359 entitled "Link systems and articulation mechanisms for remote manipulation of surgical or diagnostic tools," filed Jun. 15, 2010.

Cox, James; The minimally invasive Maze-III procedure; Operative Techniques in Thoracic and Cardiovascular Surgery; vol. 5; No. 1; pp. 79-92; Feb. 2000.

Simha et al.; The elctrocautery maze—how I do it; The Heart Surgery Forum; vol. 4; No. 4; pp. 340-345; Aug. 23, 2001.

Prasad et al.; Epicardial ablation on the beating heart: progress towards an off-pump maze procedure; The Heart Surgery Forum; vol. 5/ No. 2; pp. 100-104; Jun. 27, 2001.

Hegeman et al; U.S. Appl. No. 11/787,543 entitled "Tool with articulation lock," filed Apr. 16, 2007.

Hinman, Cameron; U.S. Appl. No. 11/787,607 entitled "Tool with rotation lock," filed Apr. 16, 2007.

Hinman et al; U.S. Appl. No. 11/787,599 entitled "Tool with end effector force limiter," filed Apr. 16, 2007.

Hegeman et al; U.S. Appl. No. 11/787,201 entitled "Articulating tool with improved tension member system" filed Apr. 16, 2007.

Hinman et al.; U.S. Appl. No. 12/725,377 entitled "Articulating mechanism with flex-hinged links," filed Mar. 16, 2010.

\* cited by examiner

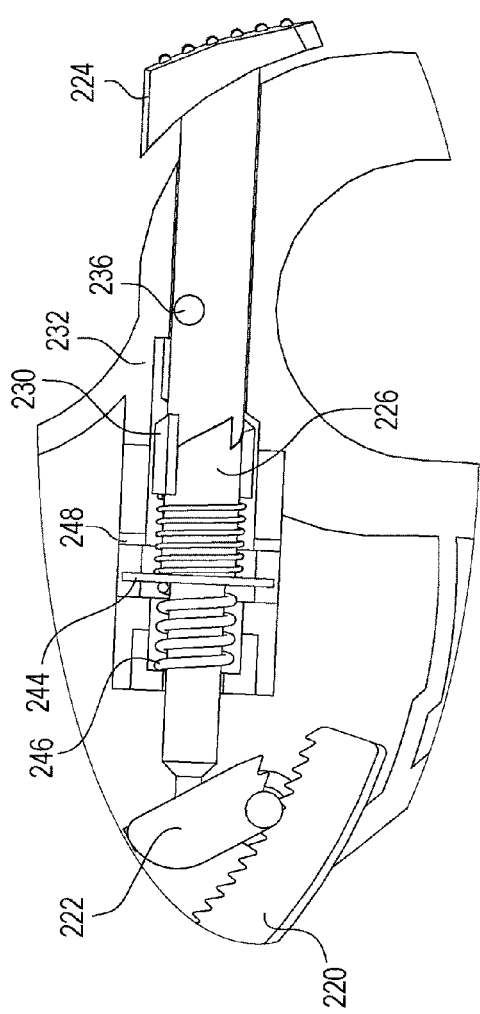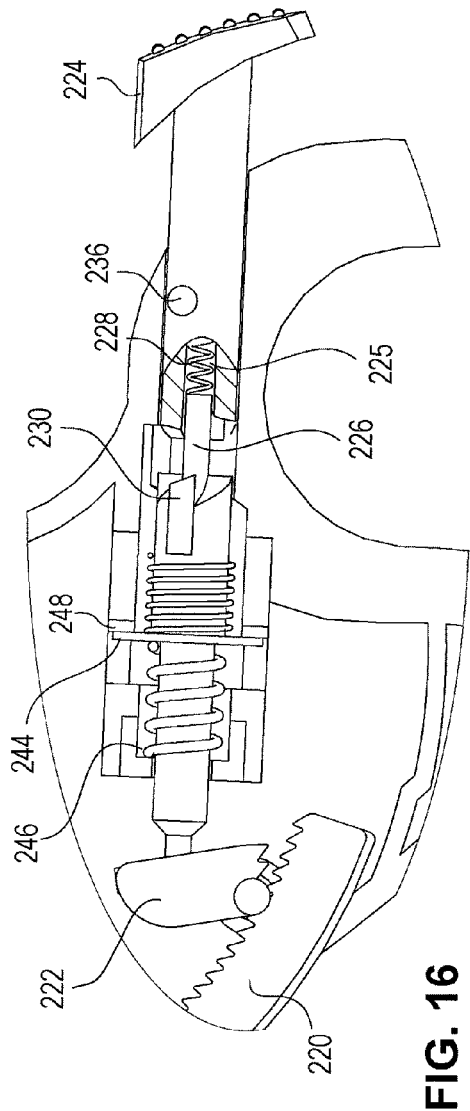
FIG. 15
FIG. 16

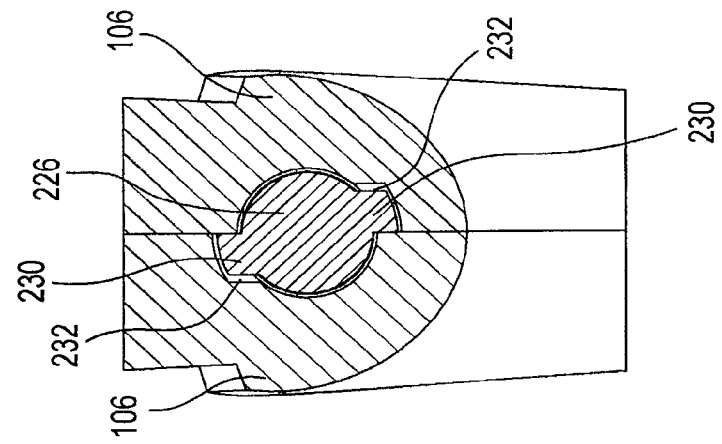
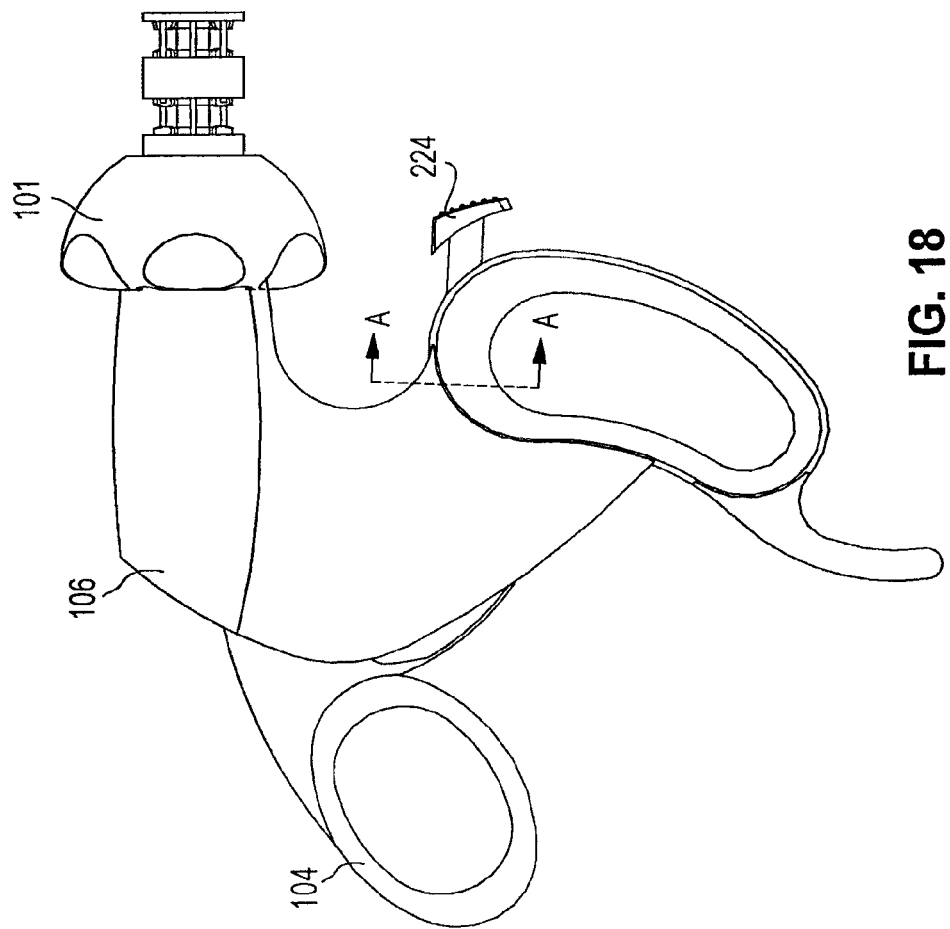
FIG. 18
FIG. 19

TOOL WITH MULTI-STATE RATCHETED END EFFECTOR

CROSS REFERENCE TO RELATED APPLICATIONS

This application is related to the following concurrently filed U.S. patent applications: U.S. application Ser. Nos. 11/787,543, 11/787,599, 11/787,607, and 11/787,608.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to tools with end effectors whose actuators may be operated in multiple different operation states.

BACKGROUND OF THE INVENTION

The popularity of minimally invasive surgery has been growing rapidly due to its association with decreased complication rates and post-surgical recovery times. The instruments employed are generally hand-operable and typically include a handle, a shaft that may or may not be rotatably attached to the handle, a rotation knob rigidly fixed to the proximal end of the shaft near the handle in instances where the shaft is rotatably attached to the handle, and a tool or end effector attached to the distal end of the shaft. To manipulate the instruments, they are held at the handle and typically pivoted about a pivot point defined by the entry incision, i.e., the incision made in the abdominal wall for laparoscopic procedures. The end effector may also be rotated about the shaft axis, as for example, by rotating a rotation knob, if present. In use, these instruments have limited control and range of motion and become physically taxing as the length of the procedure increases.

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cable. As with conventional instruments used in minimally invasive surgery, rotation of the shaft and end effector with respect to the handle is an important feature of cable and link type instruments to aid with dissecting, suturing, retracting, knot tying, etc. Ergonomic, flexible, and intuitive mechanisms that facilitate manual control of the end effectors of such instruments are also important factors as medical procedures become more advanced, and as surgeons become more sophisticated in operating abilities. Further improvements in the features and design of surgical instruments are desirable.

SUMMARY OF THE INVENTION

Embodiments of the invention include a shaft having a proximal end and a distal end, an end effector at the distal end of the shaft, a movable end effector actuator at the proximal end of the shaft and operably connected to the end effector, and an actuator movement controller operably connectable to the end effector actuator. The actuator movement controller includes a user-activated state changer that is changeable among several states. These states include ones in which the movement controller is (1) enabled and engaged with the end effector actuator to prevent movement of the end effector actuator in at least one of two opposing directions, (2) enabled and disengaged from the end effector actuator to permit movement of the end effector actuator in a first direction and a second direction opposite to the first direction in response to continuous user input via the state changer, and (3) disabled to permit movement of the end effector actuator in a first direction and a second direction opposite to the first direction in the absence of user input via the state changer. In some embodiments, the first state (enabled and engaged) may prevent movement of the end effector actuator in both directions.

In some embodiments the end effector includes jaws. In some embodiments the actuator movement controller includes a ratchet. In some embodiments the state changer includes a movable trigger. In some embodiments with a trigger, the state changer further includes a toggle operatively connected to the trigger so as to be movable with the trigger and to be rotatable with respect to the trigger. In some of the embodiments with a toggle, the toggle is operatively connected to the trigger so as to move with the trigger without rotating with respect to the trigger when the movement controller is enabled.

In some embodiments where the toggle is so-connected to the trigger, surgical instrument further includes a handle at the proximal end of the shaft, and the trigger is supported by the handle, and is movable with respect to the handle. The toggle is disposed within the handle, and the trigger may include a toggle-camming surface and the toggle may include trigger-camming surface complementary-to and engagable with the trigger surface. The handle of some embodiments may include a toggle guide, operatively connected to the toggle, to guide movement of the toggle. Engagement of the complementary camming surfaces of the trigger and toggle respectively, due to movement of the trigger creates a rotational force between the trigger and toggle.

Embodiments summarized immediately above may further include a wing extending radially from a toggle body, the handle toggle guide comprising a slot in which the toggle wing is disposed to prevent rotation of the toggle as the toggle moves with the trigger. The handle's toggle guide may include a handle camming surface complementary-to, and engagable with the toggle wing's camming surface such that engagement of the handle camming surface with the toggle wing's camming surface creates a rotational force between the handle and the toggle. In such embodiments, the toggle may have a range of motion, and the handle toggle guide may be adapted to prevent rotation of the toggle in a first portion of the toggle's range of motion and to permit rotation of the toggle with respect to the trigger in a second portion of the toggle's range of motion. The toggle may further include a wing extending radially from a toggle body, the handle toggle guide include a slot in which the toggle wing is disposed when the toggle is in the first portion of its range of motion, the toggle wing being outside the slot when the toggle is in the second portion of its range of motion Returning to the movable trigger, in some embodiments the trigger is movable from a first position in which the movement controller is enabled and engaged to a second position in which the movement controller is enabled and disengaged. The trigger may be further movable to a third position in which the movement controller is disabled. In such embodiments with the third position, the trigger may be further movable so as to enable and engage a disabled movement controller. The movement controller may further include a state change notifier that is operatively connected to the trigger and adapted to provide notice of an impending change in movement controller state that will be caused by further movement of the trigger. The state change notifier is adapted to provide tactile feedback to a user through the trigger of an impending change in movement controller state that will be caused by further movement of the trigger; such tactile feedback may include an increased level of resistance to movement of the trigger.

Embodiments of the invention include a shaft having a proximal end and a distal end, an end effector at the distal end of the shaft, a movable end effector actuator at the proximal end of the shaft and operably connected to the end effector, and an actuator movement controller operably connectable to the end effector actuator. The actuator movement controller may include a state changer and a biasing member. The state changer may be movable against the biasing member in response to a user input from a first state in which the movement controller is enabled and engaged with the end effector actuator to permit movement of the end effector actuator in one direction and prevent movement of the end effector actuator in an opposite direction to a second state in which the movement controller is enabled and disengaged from the end effector actuator to permit movement of the end effector actuator in a first direction and a second direction opposite to the first direction. The biasing member may be operably connected with the state changer to move the state changer from the second state to the first state when the user input ceases or diminishes.

In some embodiments, as summarized above, the state changer may be movable against the biasing member in response to a user input from the second state to a third state in which the movement controller is disabled to permit movement of the end effector actuator in a first direction and a second direction opposite to the first direction in the absence of user input via the state changer.

In some embodiments the end effector includes jaws. In some embodiments the actuator movement controller includes a ratchet. In some embodiments the state changer includes a movable trigger. In some embodiments, the controller may further include a state change notifier adapted to provide notice of an impending change in movement controller state that will be caused by further movement of the state changer. In some embodiments, the state changer has a range of motion and the biasing member includes a first spring, the state change notifier includes a second spring. In typical embodiments, the second spring has a spring constant greater than the spring constant of the first spring. The state changer may be disposed with respect to the first and second spring so as to deform the first spring during a first portion of its range of motion in the second state without deforming the second spring and to deform the second spring in a second portion of its range of motion in the second state, the second spring applying a greater force on the state changer in the second portion of its range of motion than the first spring applies on the state changer in the second portion of its range of motion.

Embodiments of the invention include a method for operating a medical instrument, the instrument including, as summarized above, an end effector at the distal end of a shaft, an end effector actuator at a proximal end of the shaft, and an actuator movement controller. The method includes, without limitation regarding order, (1) actuating the end effector by moving the end effector actuator in a first direction while engaging the actuator movement controller with the end effector actuator to prevent movement of the end effector actuator in a second direction opposite to the first direction, (2) providing a first user input to disengage the actuator movement controller from the end effector actuator to permit movement of the end effector actuator in the first and second directions during the user input, and (3) providing a further user input to disable the actuator movement controller to permit movement of the end effector actuator in the first and second directions in the absence of user input via the state changer.

In some embodiments, providing the first user input includes moving a trigger. More specifically, moving the trigger may include moving the trigger a first distance and providing the further user input may include moving the trigger to a second distance beyond the first distance.

The step of providing user input may further include providing notice that further user input will disable the actuator movement controller. In some embodiments, prior to the step of providing a further user input, the method further may include providing notice that further user input will disable the actuator movement controller, and such providing notice may include providing a tactile sensation to the user.

Providing the first user input may also include moving the trigger a first distance, providing the further user input may include moving the trigger to a second distance beyond the first distance, the step of providing notice comprising providing increased resistance to trigger movement after moving the trigger the first distance but prior to moving the trigger the second distance.

Before providing the further user input, the method further may include removing the first user input to re-engage the actuator movement controller with the end effector actuator to prevent movement of the end effector actuator in the second direction. Providing the first user input may include moving a trigger and removing the first user input may include releasing the trigger.

In some embodiments, the method operating a medical instrument may further include providing a subsequent user input after the further user input to re-enable the actuator movement controller. Some embodiments of the method further include ceasing the further uset input prior to providing the subsequent user input. Finally, providing the first user input may include moving the trigger a first distance, providing the further user input may include moving the trigger to a second distance beyond the first distance, ceasing the further user input may include releasing the trigger, and providing the subsequent user input may include moving the trigger.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIG. 15 is an exposed view of the multi-state ratchet mechanism within the handle as in FIG. 12; in this view, the ratchet is in a disabled state.

FIG. 16 is an exposed view of the multi-state ratchet mechanism within the handle as in FIG. 12; in this view, the ratchet is still in a disabled state, but the trigger has been fully released.

FIG. 18 is a simplified side view of the handle showing a trigger; the toggle is located immediately proximal to the trigger (not seen); the position labeled with letters "A" identifies the position of a cross-section detail shown in FIG. 17.

FIG. 19 is a cross-sectional detail, as indicated in FIG. 18, showing the proximal portion of the toggle within a compartment of the handle, with toggle wings in handle slots.

DETAILED DESCRIPTION OF THE INVENTION

Figure 1:
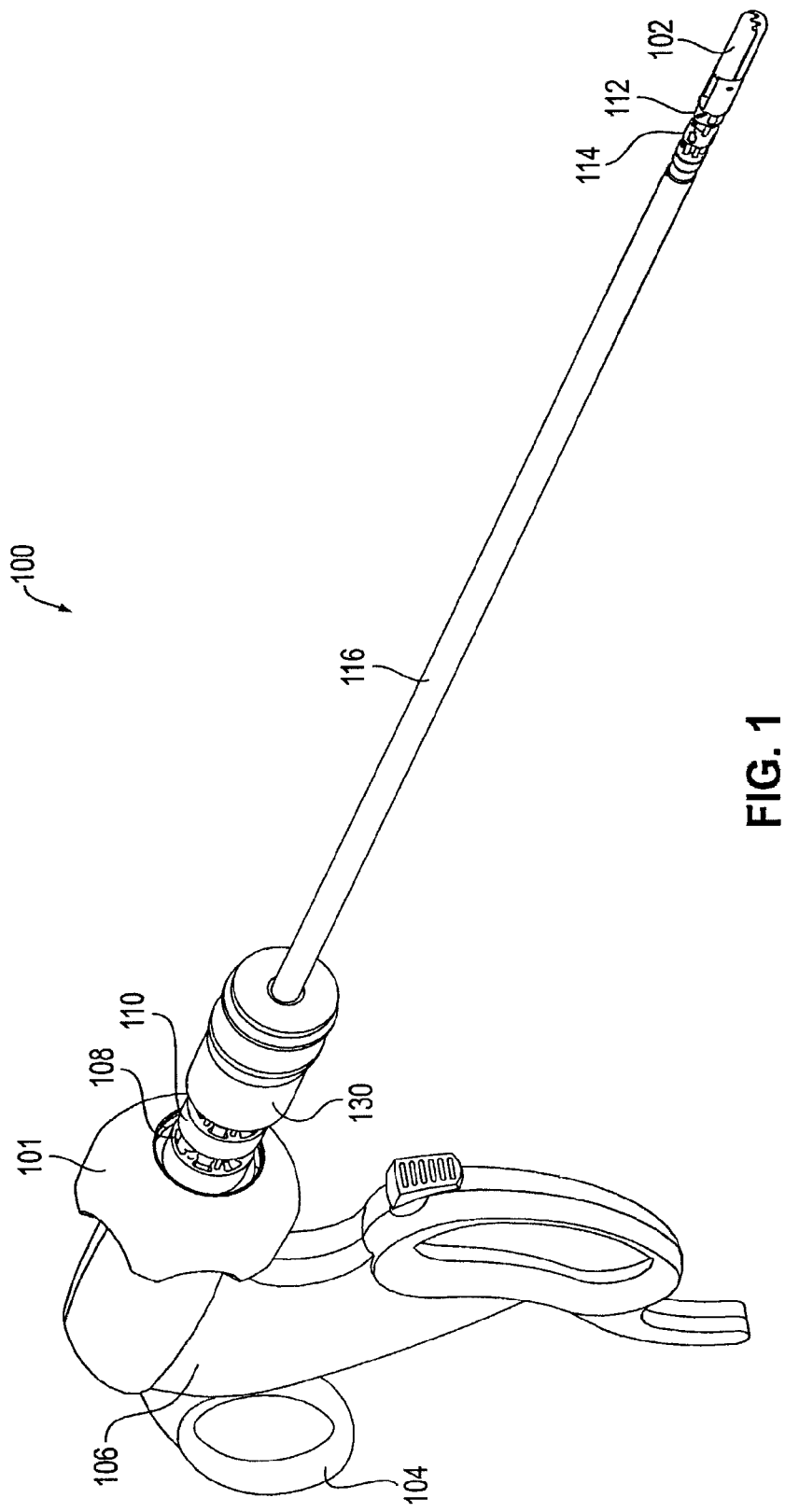
FIG. 1 is a front perspective view of an articulatable surgical tool.

Steerable articulating instruments are described in U.S. Pat. No. 7,090,637; US 2005/0107667; US 2005/0273084; US 2005/0273085; and US 2006/0111209, US 2006/0111210. The articulating mechanisms of the tools described in those publications use multiple pairs of segments or links controlled, e.g., by multiple sets of cables. Depending upon the specific design of the device, the links can be discrete segments (as described, e.g., in U.S. Pat. No. 7,090,637) or discrete portions of a flexible segment (as described, e.g., in US 2005/0173085). The instrument may also include steerable or controllable links separated by bushings, e.g., as described in US 2005/0273084 US 2006/0111209 and US 2006/0111210, or any by any other type of link.

When using such articulating instruments, a user may manipulate the proximal end of the instrument, thereby moving one or more proximal links of the articulation mechanism. This movement results in relative movement of the distal link(s) corresponding to the proximal link(s). It may at times be desirable to lock or otherwise maintain the straight or bent shape of the instrument, as provided by the ability to articulate. In certain embodiments of this invention, the shape of the instrument is maintained by preventing movement of at least one of the proximal links with respect to the rest of the instrument.

Many instruments, including articulating instruments, have distally-located end effectors (e.g., a set of jaws) that are controlled by proximally-located movable end effector actuators (e.g., a moveable portion of the handle, or a thumbpiece). In typical embodiments of the moveable actuator, movement is possible in two directions, typically opposing or reciprocal. In some embodiments, the end effector actuator has various operation states in which movement is permitted or prevented by a movement controller, such as a ratchet mechanism that has various operating states. The operating states of the end effector actuator are, of course, reflected in the operating state of the end effector.

Accordingly, certain embodiments of this invention provide methods and devices for changing the operational state of an end effector actuator between a first state (1) in which movement of the actuator is prevented in at least one of two opposite directions; a second state (2) in which the actuator is permitted to move in two directions in response to continuous user input to a state changer; and a third state (3) in which the actuator is permitted to in two directions in the absence of user input to a state changer. Regarding state 1, wherein the ratchet mechanism is engaged, in some embodiments, the movement is disallowed in both directions, in other embodiments, movement is permitted in one direction, and prevented in one. The determinant of whether movement is prevented in one or both directions may be related to the steepness of the angle of mutually engaging teeth of the rack and pawl. The desirability of such variations is associated with the specific use to which the end effector is being applied.

FIGS. 1-26 show an articulatable tool 100 with an end effector 102 at its distal end and an end effector actuator 104 within a handle 106 at its proximal end. The end effector actuator 104 in typical embodiments of the tool is a movable portion of the handle, typically operated by the thumb of a user, and therefore may be referred to as a thumbpiece. Instrument 100 may be used in various contexts, including medical procedures such as a laparoscopic procedure that requires grasping or cutting within a patient.

The tool embodiments depicted herein include an ability to articulate, although some embodiments may not articulate. Articulation mechanism components include proximal articulation links 108 and 110 which extend distally from handle 106, and distal articulation links 112 and 114 extend proximally from end effector 102. Proximal link 108 is connected to and moves with handle 106. Likewise, distal link 112 is connected to and moves with end effector 102. Further details of ball and socket links suitable for use with this invention may be found in US 2005/0273084, US 2006/0111209, and US 2006/0111210. Embodiments of the presently described invention may make use of any type of link known in the art, the aforementioned specific links are merely offered as examples. An elongated shaft 116 is typically disposed between the proximal links and the distal links. Although the shaft depicted in figures herein is represented as a rigid embodiment, other shaft embodiments may be flexible.

Further with regard to features that support articulation in the depicted embodiments (FIGS. 3 and 4), a set of tension bearing members 118 is attached to proximal link 108, extends through proximal link 110, shaft 116 and distal link 114 and is attached to distal link 112. (Although not limited to cables, a typical embodiment of a tension bearing member is a cable, and cables will be commonly referred to herein, as exemplary tension bearing members.) A second set of control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, mechanisms or tension bearing members other than cables may be used to operably connect corresponding links.

Figure 2:
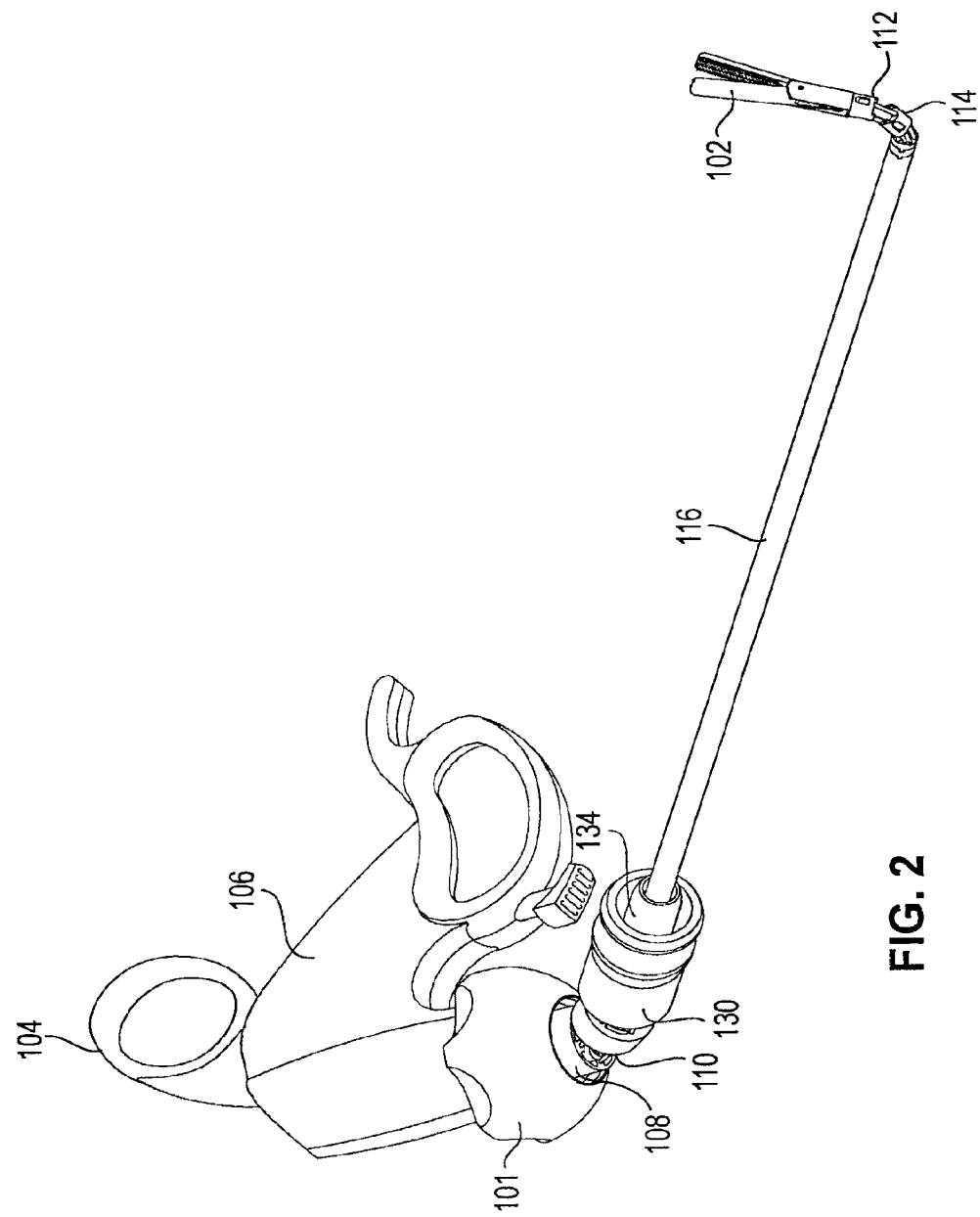
FIG. 2 is perspective view of a surgical tool in an articulated position.

As shown in FIG. 2, movement of handle 106 and proximal link 108 with respect to proximal link 110 moves end effector 102 and distal link 112 in a relative and corresponding manner. Likewise, movement of proximal link 110 with respect to shaft link 116 moves distal link 114 with respect to shaft link 116 in a relative and corresponding manner, also as shown in FIG. 2. This relative articulation movement provides a way for a user to remotely manipulate the end effector through movement of the handle.

Figure 3:
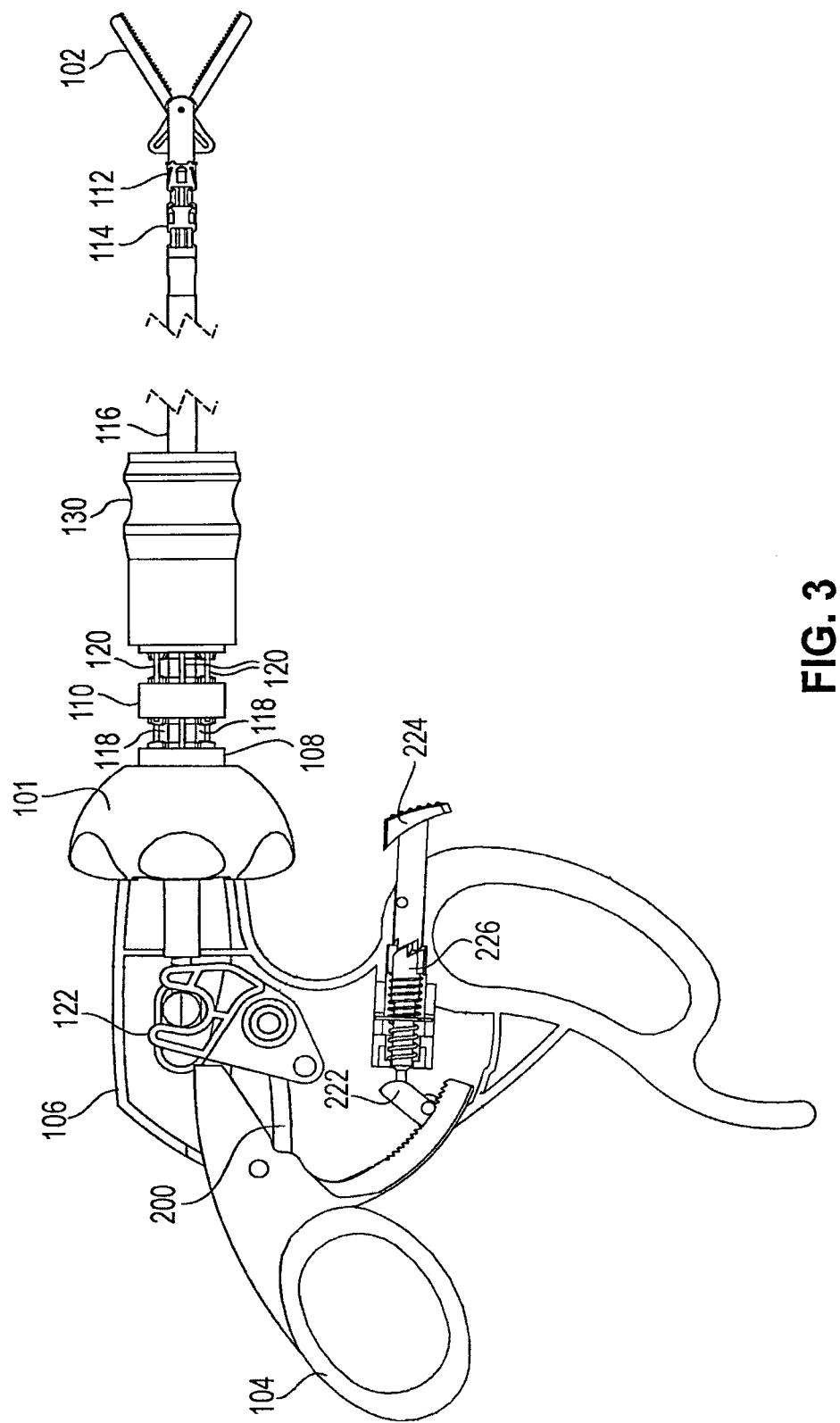
FIG. 3 is an exposed side view of a surgical tool with an end effector actuator and an end effector both in an open position.
Figure 4:
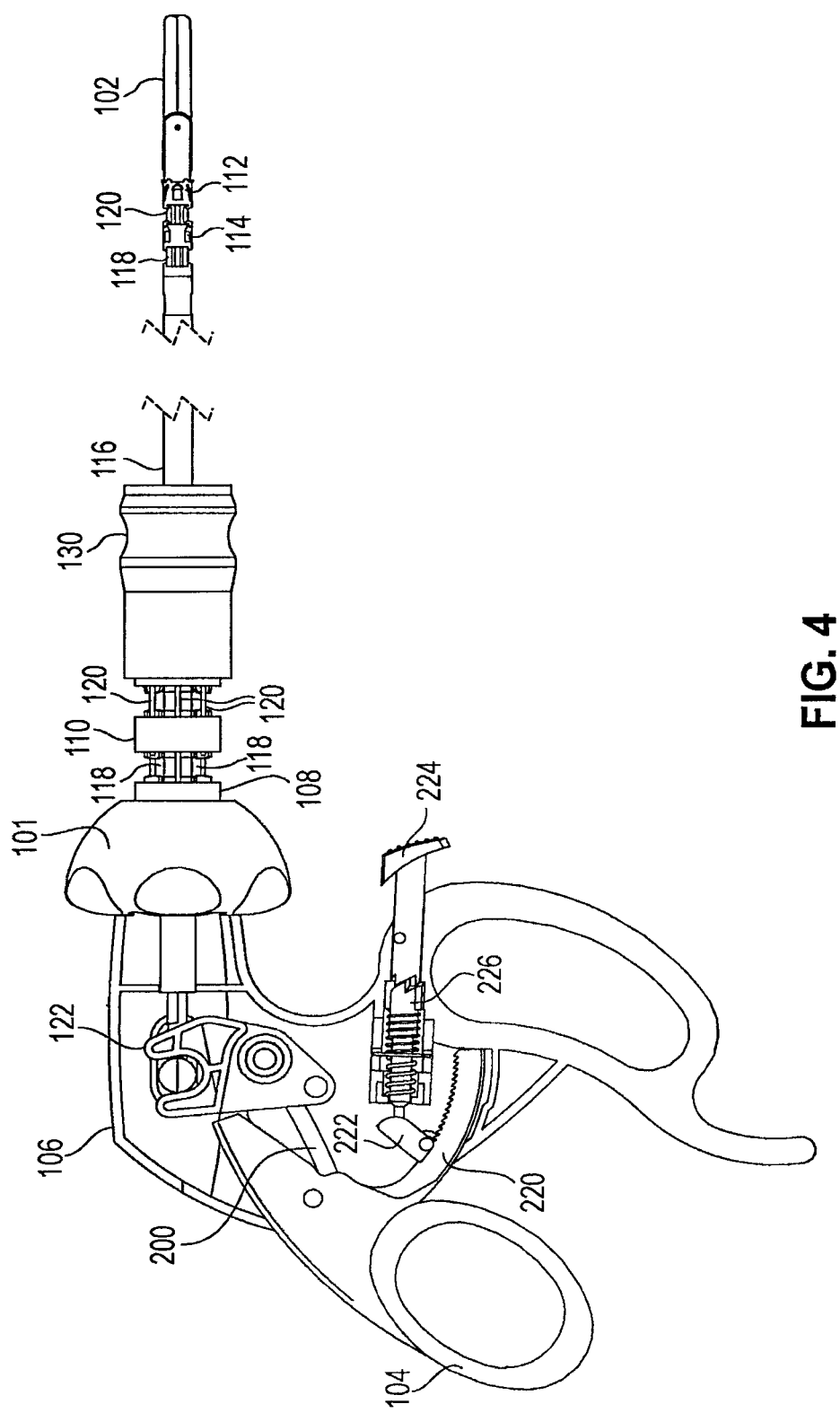
FIG. 4 is an exposed side view of a surgical tool with an end effector actuator and an end effector both in a closed position.
Figure 5:
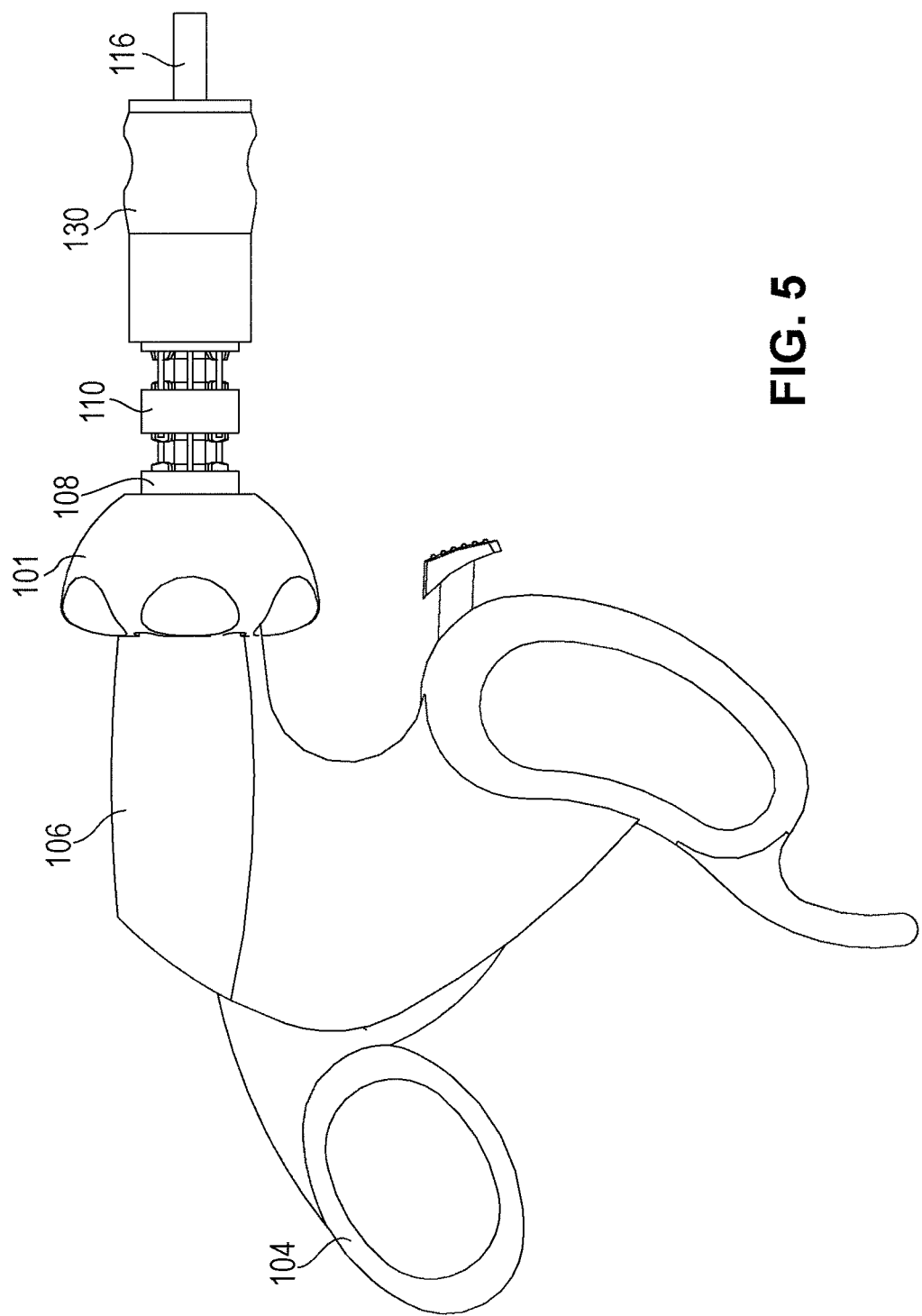
FIG. 5 is a side view of the proximal portion of a tool, showing the handle and proximal end of the shaft, with an articulation locking sleeve in a distal and unlocked position.
Figure 7:
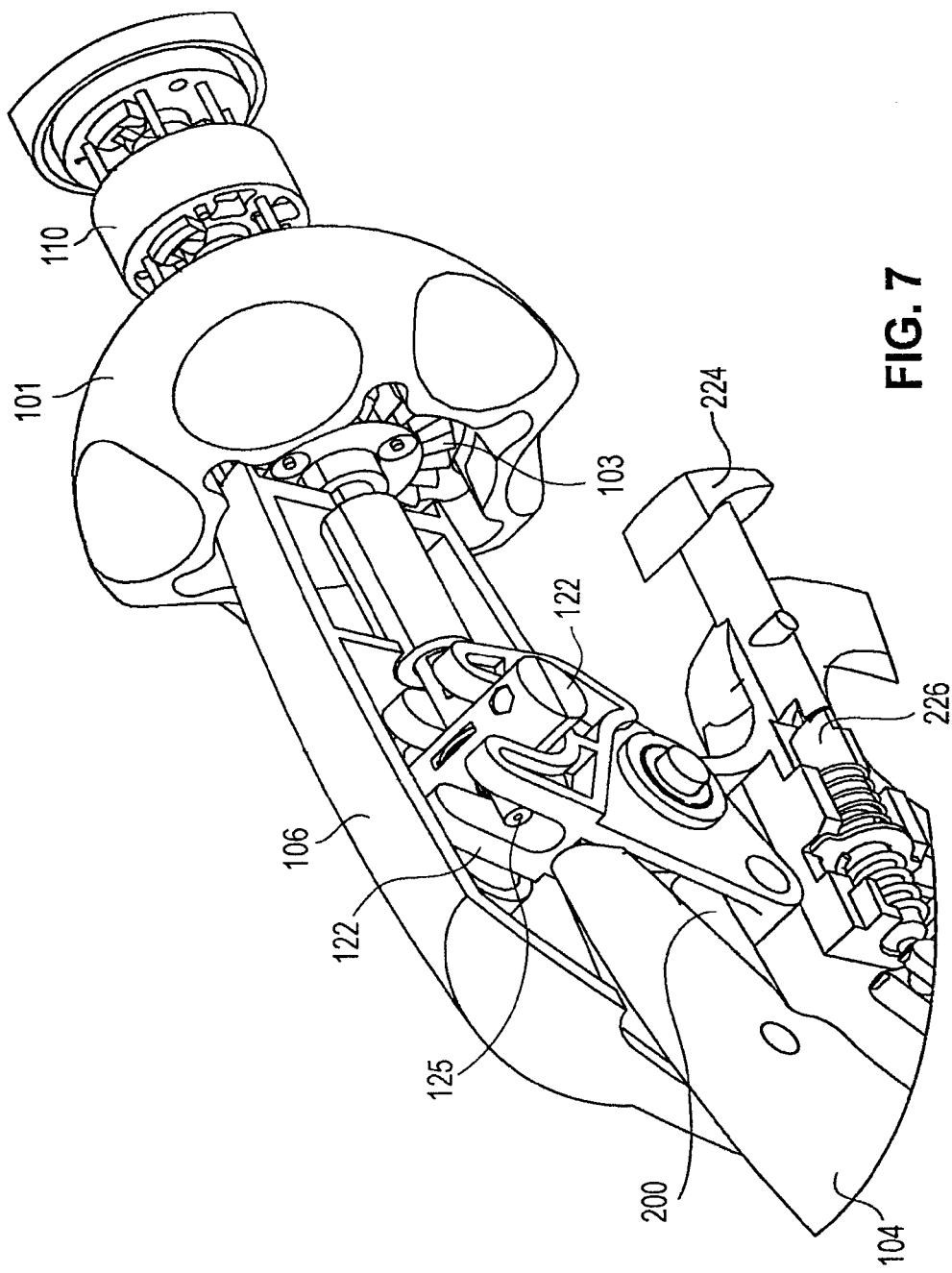
FIG. 7 is an exposed view of a portion of a tool from an overhead distal-looking perspective, the portion including the handle, locking rotation knob, and a proximal link.
Figure 9:
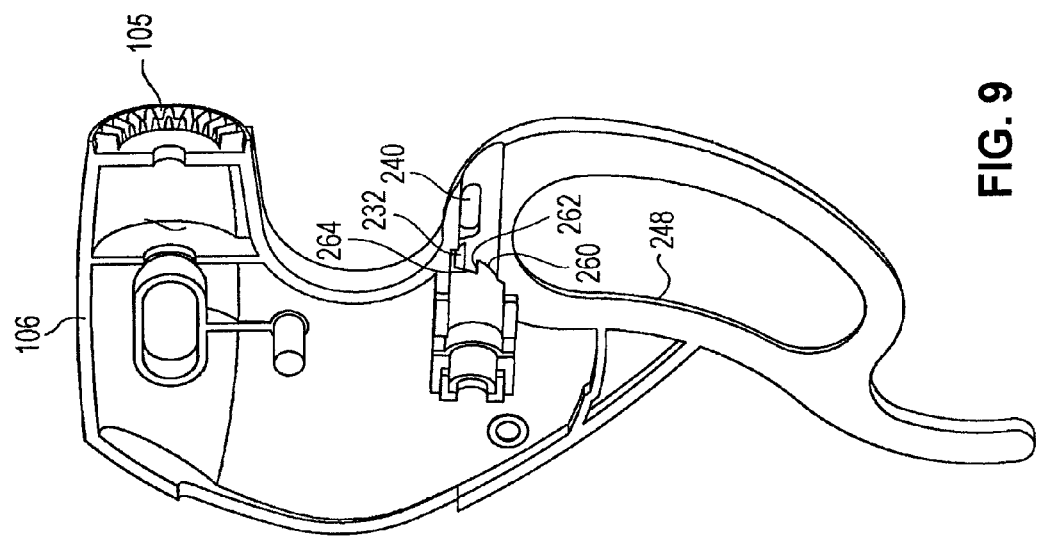
FIG. 9 is an exposed view of a handle from a proximal-looking perspective.
Figure 8:
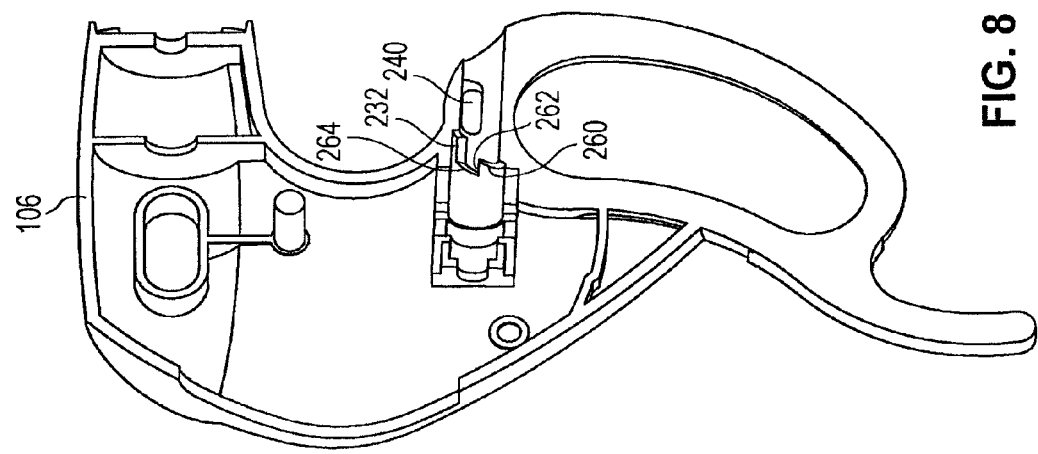
FIG. 8 is an exposed view of a handle from a distal-looking perspective.
Figure 10:
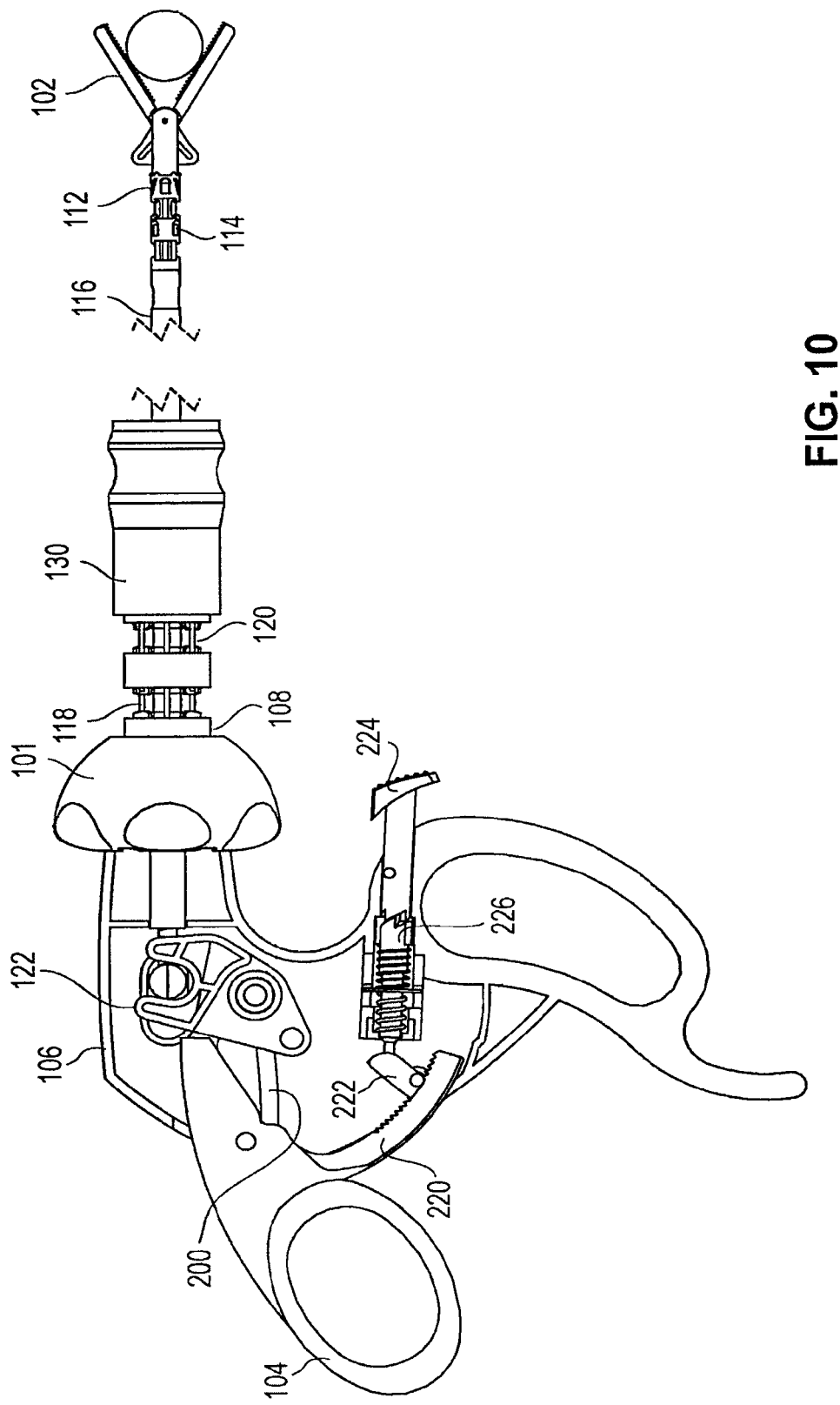
FIG. 10 is an exposed side view of a surgical tool with an end effector actuator and an end effector both in an open position, the end effector jaws embracing an object.
Figure 11:
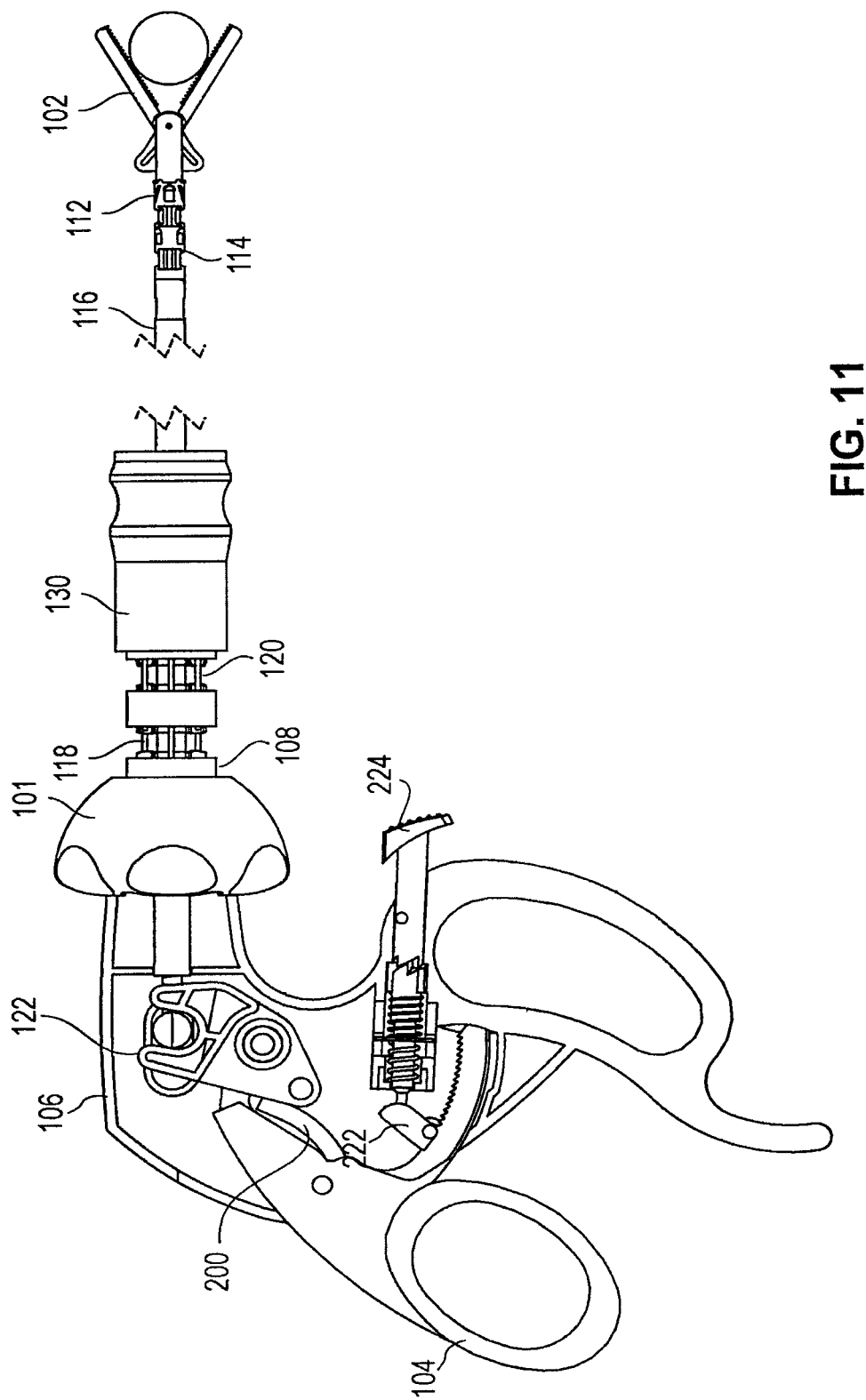
FIG. 11 is an exposed side view of a surgical tool with an end effector actuator in a closed position and the end effector in an open position, the end effect or jaws embracing an object, the force applied by the closed end effector actuator having been absorbed by a force limiter.

In the shown exemplary embodiments (FIGS. 1-4, 10, and 11) the end effector 102 is a pair of jaws. Other end effectors for any surgical or diagnostic application, or for other applications, including non-medical applications, may be used with the articulating tool of this invention. Actuation force is transmitted from end effector actuator 104 through a transmission that includes a linearly movable tension bearing member or rod 125 and a rotatable rod actuator 122, as shown in FIGS. 3, 4, and 7. In some embodiments, the tension bearing member or rod 125 is also capable of bearing a compressive load, such that an end effector can receive a compressive force transmitted by the end effector actuator.

In order to maintain a particular position of the end effector with respect to the shaft, whether the position is a straight or neutral position, or an articulated position, the articulating tool of this invention may include an articulation lock. The articulation lock embodiment described below is merely one example, numerous other embodiments are provided in the concurrently filed U.S. application Ser. No. 11/787,543, which is hereby incorporated into this application by this reference.

In the embodiment shown in FIGS. 1-6, the articulation lock includes a movable rigid sleeve 130. In the unlocked position shown in FIGS. 1-5, sleeve 130 is distal to proximal links 108 and 110. In the locked position shown in FIG. 6, however, sleeve 130 has been moved proximally to a position adjacent to and covering links 108 and 110 as well as the proximal end of shaft 116, thereby blocking relative movement between links 108 and 110 and between link 110 and shaft 116. In this locked position, relative movement between distal links 112 and 114 and between link 114 and shaft 116 is prevented as well.

Figure 6:
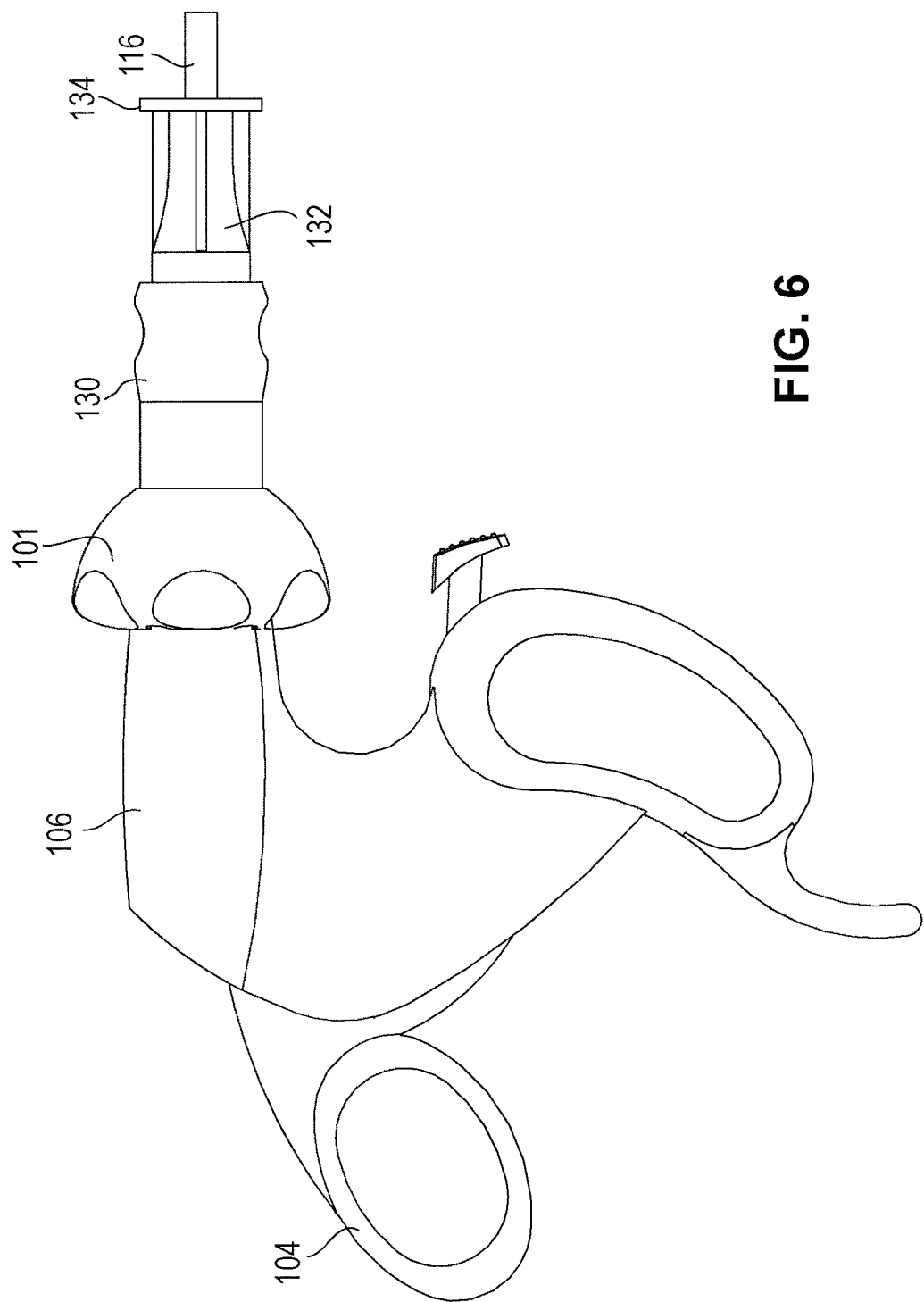
FIG. 6 is a side view of the proximal portion of a tool, showing the handle and proximal end of the shaft, with an articulation locking sleeve in a proximal and locked position.

As shown in FIG. 6, a sleeve support mechanism 132 extends proximally from shaft 116 to provide sliding support for sleeve 130. A distal stop 134 provides a limit of distal movement of sleeve 130; a similar stop (not shown) is provided on or within handle 106 to limit proximal movement of sleeve 130. Detents, ridges or other mechanisms may be provided to maintain the sleeve in its proximal or distal positions and to provide tactile feedback to the user regarding the position of the sleeve.

Some embodiments of the inventive tool with a multi-state ratchet mechanism include features that provide rotatability of end effectors, and some of these embodiments further include a rotation lock that allows or disallows such rotation. A rotation lock may comprise a locking knob 101, as can be seen in FIGS. 1-7. Other components of the depicted rotation lock include teeth 103 within the knob 101 that are visible in FIG. 7; these teeth engage the complementary teeth 105 within the handle 106 that are visible in FIG. 9. These embodiments are described in detail in concurrently filed application of Hinman and Danitz entitled "Tool with Rotation Lock", which is hereby incorporated into this application by this reference.

Some embodiments of the inventive tool with a multi-state ratchet mechanism include a force limiter that establishes an upper limit on the actuation force that may be delivered to the end effector by the end effector actuator. An embodiment of a force limiter 200 may be seen in FIGS. 3, 4, 7, 10, and 11. These embodiments are described in detail in concurrently filed application of Hinman and Bertsch entitled "Tool with End Effector Force Limiter", which is hereby incorporated into this application by this reference.

The instrument of this invention has an actuator movement controller, comprising a ratchet mechanism that controls the way that an end effector actuator (a thumbpiece, for example) and an end effector can be moved by a user. A state changer, such as a trigger 224 may be used to change among the end effector actuation states. In the embodiment shown in FIGS. 1-26, but particularly in FIGS. 12-18, and as laid out in Table 1, the instrument has three end effector actuation states: (1) a state in which the movement controller is enabled and engaged with the end effector actuator to prevent movement of the end effector actuator in at least one direction—in some embodiments movement is prevented in one direction and permitted in the other while in some embodiments movement in both directions is locked; (2) a state in which the movement controller is enabled and disengaged from the end effector actuator to permit movement of the end effector actuator in a first direction and a second direction opposite to the first direction, the disengagement by virtue of continuous user input via a state changer associated with the movement controller; and (3) a state in which the movement controller is disabled, even without user input via the state changer, to permit movement of the end effector actuator in a first direction and a second direction opposite to the first direction in the absence of user input via the state changer.

The numbering scheme of these described states (1, 2, and 3) is provided as an aid to understand the invention and its various operational states, and is in merely one of various numbering schemes that could be used. Movement through the states is cyclical, and in some sense, the cycle could be described with any state as a starting point or a "first state". As will be described further below, movement between states 1 and 2 is "reversible", and can go in either direction, from state 1 to state 2, and from state 2 to state 1. Movement from state 2 to state 3, however, has a unidirectionality (2 to 3), and is not reversible. Similarly, movement from state 3 (back) to state 1 is not reversible. The "reversibility" of the change between states 1 and 2 provides benefit to the user for the combination of subtlety and precision that it brings to the operation of the tool. Subtlety comes from the intuitiveness of the physical maneuver and for the minimal burden on attention and physical effort that the maneuver requires; precision comes from the on/off nature of the operational impact of the ratcheting lock.

Some embodiments provide a movement controller using a ratchet mechanism that, when engaged, permits the end effector actuator to be moved in one direction (e.g., to close a pair of jaws) while preventing the end effector actuator to move in the other direction (to, e.g., maintain the jaws in their closed state). As shown in FIGS. 3, 4, 10, and 11, for example, the ratchet is formed from a rack of teeth 220 extending from end effector actuator 104. A movable pawl is rotatably mounted in handle 106. In other embodiments, the teeth of the rack 220 may be configured with a steepness of angle (not shown) such that the engaged state prevents movement of the pawl with respect to the rack in either direction. In other embodiments, prevention of movement in either direction by the engaged ratchet is provided by other engagement features well known in the art, such as pins or friction surfaces. A user may change the operation state of the ratchet by operating a state changer or trigger 224 which connects to pawl 222 through a toggle 226.

Figure 22:
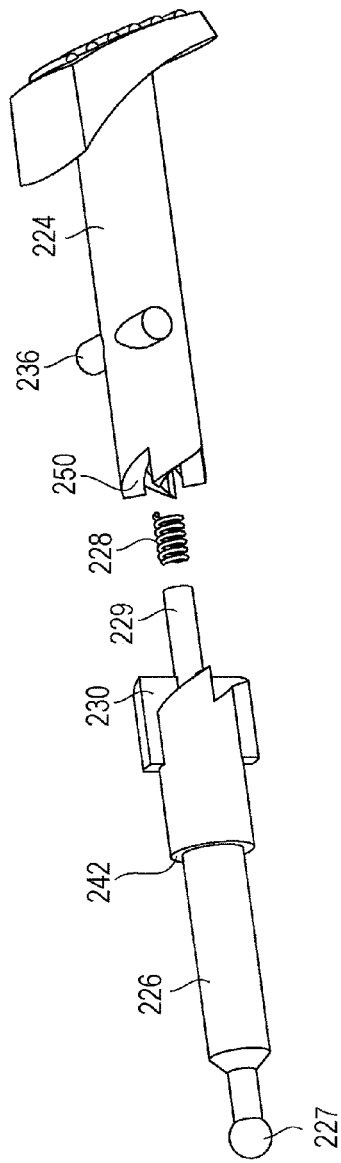
FIG. 22 shows a trigger (right) and toggle (left) aligned but in an exploded view, exposing a small trigger spring.
Figure 23:
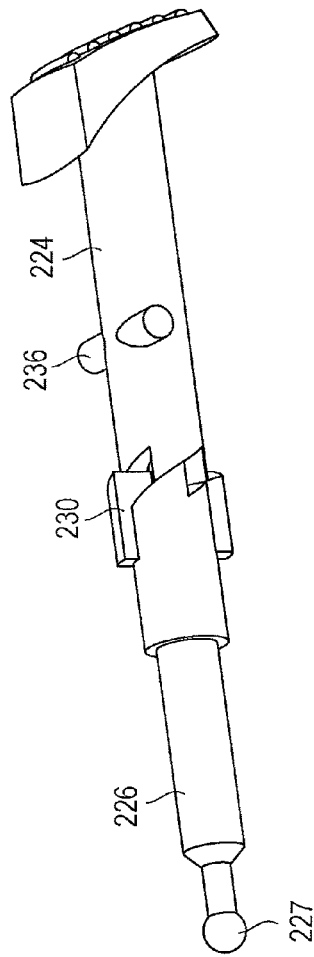
FIG. 23 shows a view of a trigger and toggle with their camming surfaces partially engaged, when the toggle is held in slots of the handle.
Figure 24:
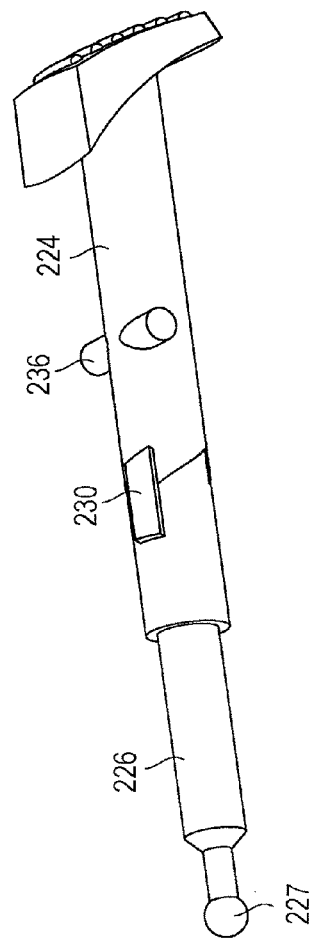
FIG. 24 shows a view of a trigger and toggle with their camming surfaces rotated out of the handle slots such that their camming surfaces are fully engaged.
Figure 25:
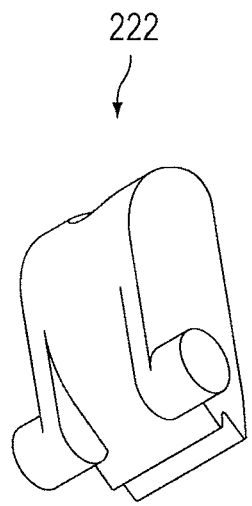
FIG. 25 is a perspective view of a pawl.
Figure 26:
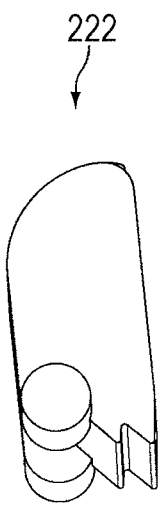
FIG. 26 is a side view of a pawl.

Details of the ratchet mechanism and ratchet state changer (e.g., a trigger and a toggle) are shown in FIGS. 12-26. Toggle-located features and trigger-located features may also be seen more clearly in FIGS. 21 and 22, respectively. FIGS. 22-24 provide detail on both the trigger 224 and toggle 226 in the context of their mutual alignment and interaction. FIGS. 18 and 19 provide some detail on the state changer (comprising toggle 226) and its location within—and interaction with the handle 106. FIGS. 25 and 26 provide detail on an embodiment of a pawl 222 that is engaged by the toggle 226. FIGS. 12-18 depict a cycling of an embodiment of a multi-state ratchet or movement controller through its various operational states. These operational states along with the status of various of its components are also shown in Table 1.

Figure 12:
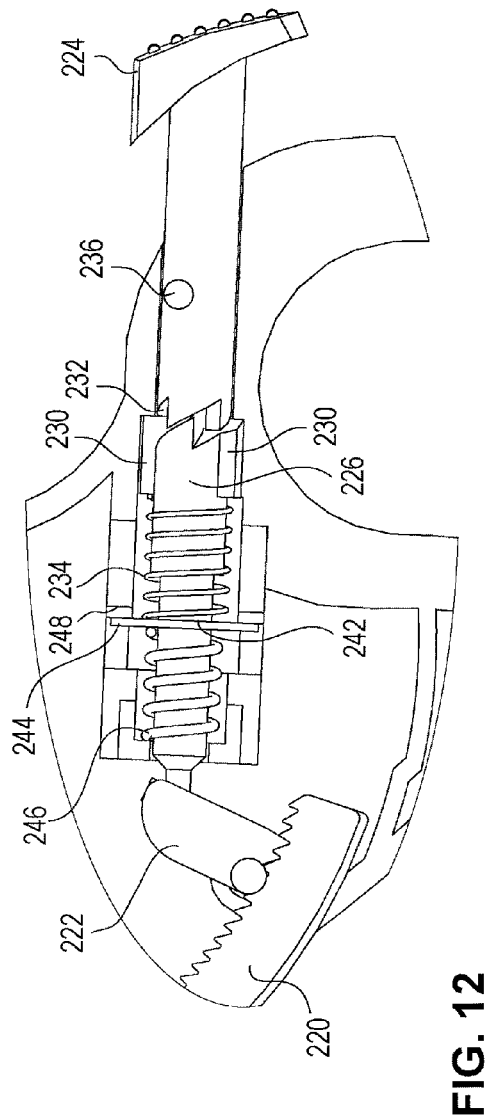
FIG. 12 is an exposed view of the multi-state ratchet mechanism within the handle, showing from right (distal) to left (proximal), a trigger, toggle, pawl, and rack; in this view, the ratchet is in its enabled and engaged state.

In FIG. 12, the ratchet is in its enabled and engaged state, with the trigger fully extended distally, or outwardly from the handle. In this state, there is little or no actuation force being applied to trigger 224 by a user, and a trigger spring 228 disposed in an internal channel 225 formed in trigger 224 (only visible in cut-away portion of FIG. 16) biases trigger 224 distally away from a distal extension 229 of toggle 226. In some embodiments, the dimensions of the trigger 224 and toggle 226 are such that in this state an optional gap occurs in

TABLE 1

Overview of Operational States of the Movement Controller (Multi-state Ratchet) of One Embodiment and Associated Aspects

| state | end effector (jaws) status* | state changer (trigger) status | springs' status | toggle rotation | movement controller (ratchet) state | |
|---|---|---|---|---|---|---|
| 1 | jaws movement is prevented in at least one direction** | trigger is released | both springs expanded | 0° | enabled | engaged |
| 2 | jaws can be closed and opened | trigger is partially depressed | light spring compressing | | enabled | disengaged "temporarily" or "reversibly", i.e., can be re-engaged by trigger release |
|   |   | further trigger depression meets greater resistance | light spring compressed heavy spring compressing (i.e., state change notifier is providing tactile feedback of imminent change) | | | |
| 3 | jaws can be closed and opened | trigger is fully depressed | both springs fully compressed | 45° | disabled | disengaged stably |
|   |   | trigger is released | both springs expanded | 90° | | |
|   |   | trigger is fully depressed | both springs fully compressed | 135° | | |
| back to 1 | See State 1, above | see State 1 | see State 1 | 180° | see State 1 | see State 1 |

*The moveability status of the end effector (i.e., jaws) also applies to the moveability of an end effector actuator, such as a thumbpiece operated by the user.
**The movement prevention may either be one-way (i.e., closing allowed, opening prevented) or two-way (opening and closing both prevented), depending on the nature of the engagement between the ratchet's rack and the pawl.

channel 225 (not shown) between trigger 224 and toggle 226 simply for the purpose of reducing occurrence of the trigger vibrating in response to movements of the pawl.

Toggle 226 has a pair of wings 230. In the enabled and engaged state, shown in FIG. 12, wings 230 are disposed in a pair of corresponding slots 232 formed in handle 106. (A cross-section of the toggle and handle in this state is shown in FIG. 19.) The proximal end 227 of toggle 226 engages pawl 222.

Figure 13:
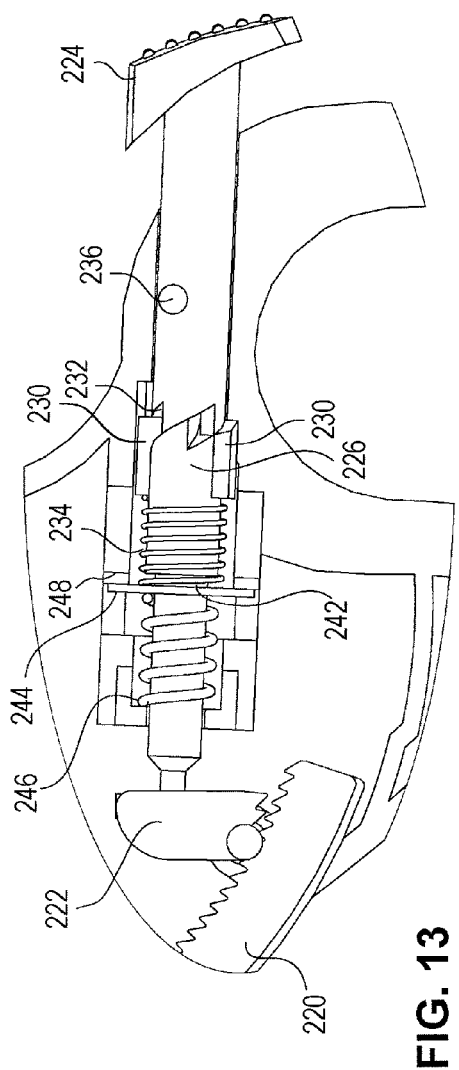
FIG. 13 is an exposed view of the multi-state ratchet mechanism within the handle as in FIG. 12; in this view, the ratchet is in its enabled but disengaged state.

As shown in FIG. 13, the ratchet is still enabled, but it has become temporarily or reversibly disengaged by the trigger being partially depressed, per the second of three states as described above. As the trigger 224 is depressed and moved proximally by a user, trigger 224 engages toggle 226, and both elements move proximally against the operation or bias of a first toggle spring 234. A pair of stems 236 extend laterally and about midway from trigger 224, and ride in corresponding channels 240 formed in handle 106 (see FIGS. 8 and 9) to guide the linear motion and to prevent rotation of trigger 224. In the position shown in FIG. 13, the ratchet is in the enabled-but-disengaged state in which the user may freely move end effector actuator in both directions so long as the user continues to hold the trigger 224 depressed. The toggle's wings 230 are still in their handle slots 232, and if the user releases trigger 224, the toggle (and trigger) will move distally under the operation of spring 234 to re-engage the ratchet and return to the enabled and engaged state shown in FIG. 12.

By way of reviewing the operational status of the ratchet mechanism in this second state, several aspects are notable. The ratchet is temporarily disengaged by virtue of the teeth of the rack and the teeth of the pawl not being engaged. The disengagement is maintained as long as the user provides an input force that maintains the trigger in a partially depressed position. The disengagement is temporary (or provisional or reversible) inasmuch as the user can release the trigger to its biased outward position, whereupon the ratchet returns to its first state, as described above, of being engaged. Finally, the releasing and partially depressing of the trigger to go back and forth between the first state (FIG. 12) and second state (FIG. 13) is repeatable.

In FIG. 13, a second toggle spring 246 biases a ring 244 distally against a shoulder 248 formed in handle 106. If instead of releasing the trigger, the user continues to push trigger 224 proximally from the position shown in FIG. 13, a proximally-facing shoulder 242 on toggle 226 engages ring 244 and moves it against the bias provided by spring 246. In this embodiment, spring 246 is stiffer (i.e., it has a greater spring constant) than spring 234; the user will therefore receive tactile feedback in the form of increased resistance to further trigger pushing as soon as toggle shoulder 242 pushes ring 244 proximally, as shown in FIG. 14.

Figure 14:
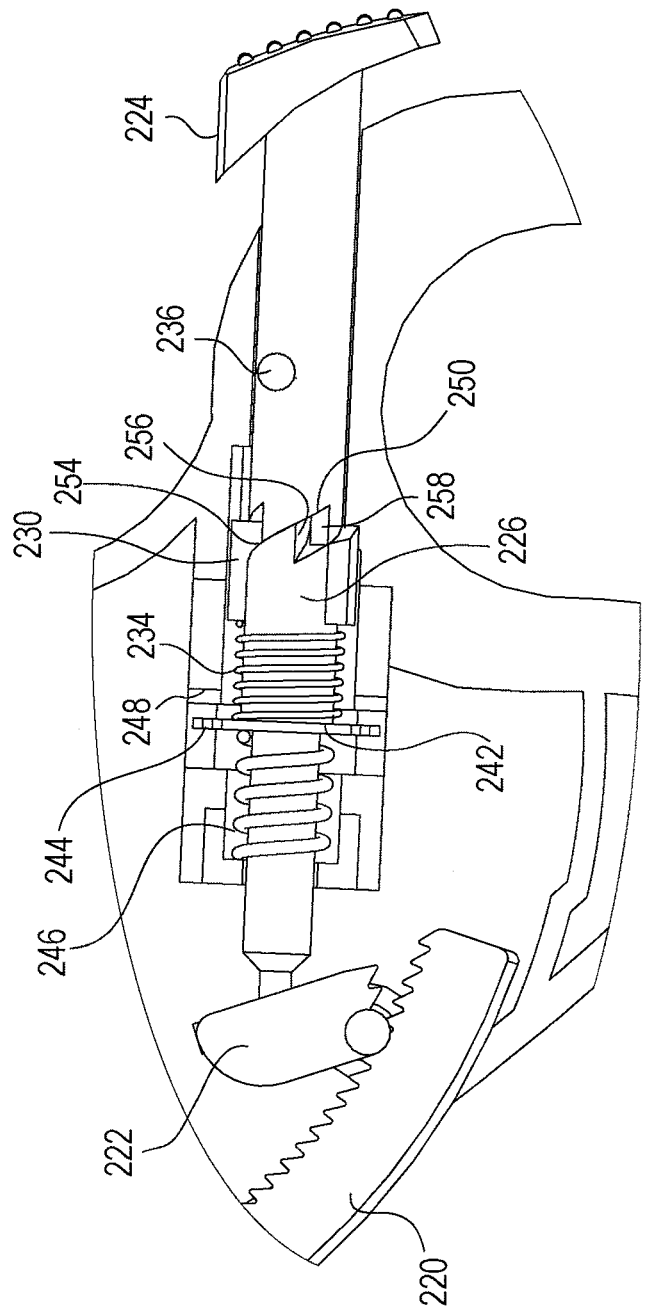
FIG. 14 is an exposed view of the multi-state ratchet mechanism within the handle as in FIG. 12; in this view, the ratchet is still engaged and disabled, but increased resistance provides the user with an indication that further depression of the trigger will change the state of the ratchet from enabled to disabled.
Figure 17:
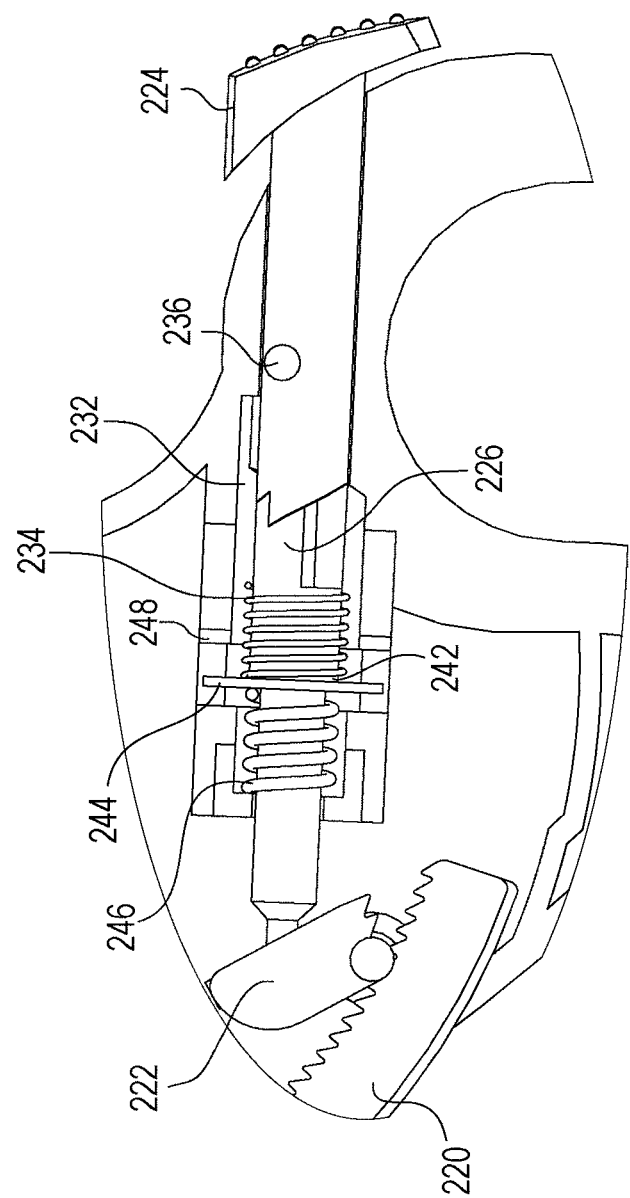
FIG. 17 is an exposed view of the multi-state ratchet mechanism within the handle as in FIG. 12; in this view, the ratchet is still in a disabled state with the trigger depressed such that when it is released the ratchet will return to the enabled and engaged state depicted in FIG. 12.
Figure 21:
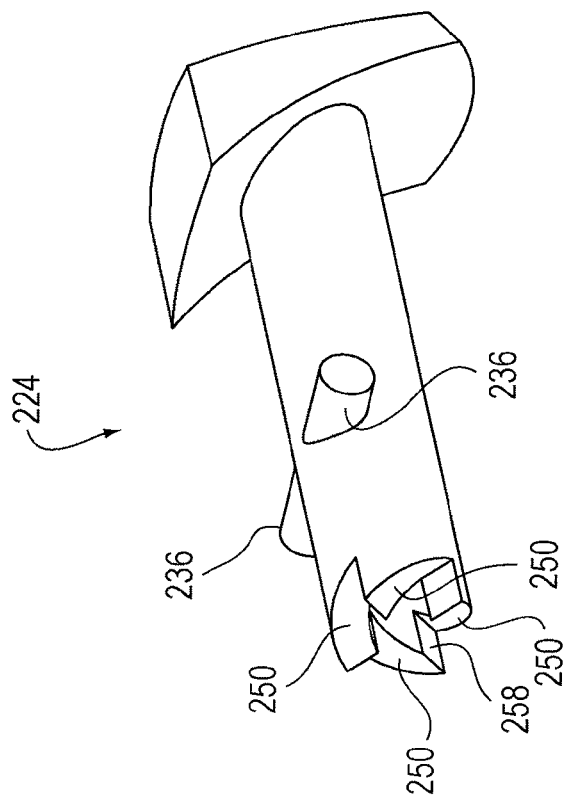
FIG. 21 is a side view of a trigger from a slightly distal-looking perspective, showing camming surfaces that engage the toggle and stems that engage the handle.
Figure 20:
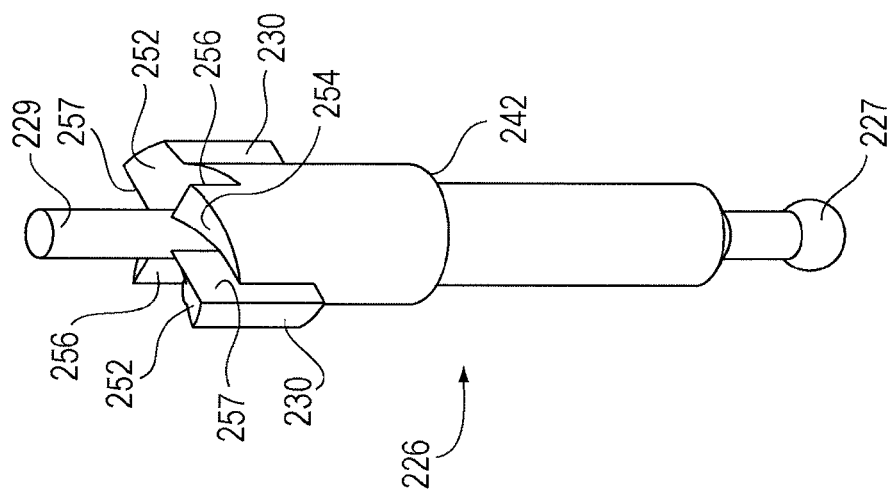
FIG. 20 is a side view of a toggle in a vertical orientation, the distal- and trigger engaging portion at the top, and the pawl-engaging portion below.

While the ratchet state in FIG. 14 is still enabled but disengaged (the second state as described above) the increased resistance provides the user with an indication that depressing the trigger further will change the state of the ratchet from enabled to disabled, as further described below. The ratchet mechanism in FIG. 14, by being in the second state (enabled and disengaged, as in FIG. 13), will still return to the first state (enabled and engaged) upon release of the trigger to its biased distal position. The new aspects of the state depicted in FIG. 14 (vs. FIG. 13) involve the trigger being yet further depressed, and the greater resistance thereby encountered by the user, which is perceived as a tactile feedback. The greater resistance is a manifestation of a state change notice provided by the state change notifier comprising spring 246. In this embodiment, the information provided by the state change notice is that the mechanism is nearly ready to move into a disabled state (the third state, as described above), wherein the ratchet is stably disengaged, and unable to passively revert to the first state.

FIGS. 15 and 16 depict the ratchet mechanism at different points in the third state, wherein the ratchet is disabled, and ultimately stably disengaged. FIG. 15 shows the toggle transitioning to the stably disengaged state as shown in FIG. 16. In FIG. 15, toggle 226 has been pulled proximally sufficiently to enable wings 230 to leave slots 232. Trigger 224 has four identical helical camming surfaces 250 on its proximal end which engage with four corresponding camming surfaces on the distal end of toggle 226. The four camming surfaces are of two kinds, though identical in slope: two camming surfaces 252 on wings 230, and two camming surfaces 254 on the enlarged shaft portion of toggle 226. Camming surfaces of the toggle 226 and trigger 224 are most easily seen in FIGS. 20 and 21, respectively. In the enabled and engaged state, shown in FIG. 12, and the enabled and disengaged state, shown in FIGS. 13 and 14, the longitudinal shoulder 256 or 257 at the end of each toggle camming surface is offset from the longitudinal shoulders 258 at the end of each trigger camming surface. Once wings 230 leave slots 232, however, toggle 226 is free to rotate under the camming interaction of surfaces 250 against surfaces 252 and 254. Toggle 226 will rotate 45° until the toggle longitudinal surfaces 256 and 257 meet the trigger longitudinal surfaces 258, as shown in FIG. 15.

When the user releases trigger 224 from the position shown in FIG. 15, the toggle and trigger move distally together until camming surfaces 252 on toggle 226 engage two camming surfaces 260 formed on the inside of handle 106 (seen best in FIGS. 8 and 9) that cause the toggle to rotate another 45° (to reach a point of 90° rotation from the reference point of the first state) until longitudinal surfaces 257 meet corresponding handle longitudinal surfaces 262. The handle camming surfaces hold toggle 226 and prevent further distal movement from this position; trigger 224 continues to move distally under the action of spring 228, as shown in FIG. 16. In this state, the ratchet is disengaged, the trigger 224 is fully released and distal, and the user may freely move end effector actuator 104 (and consequently the end effector or jaws 102) in either direction.

To return the ratchet to the enabled states, the user depresses trigger 224 again to move trigger camming surfaces 250 against toggle camming surfaces 252 and 254. When proximal movement of trigger 224 moves toggle 226 sufficiently proximal for the toggle's longitudinal surfaces 257 to clear the handle longitudinal surfaces 262, the camming action between the trigger and toggle once again rotates the toggle 45° to the state shown in FIG. 17. When the user releases trigger 224, engagement of toggle camming surfaces 252 with two other camming surfaces 264 formed in handle 106 causes another 45° rotation of toggle 226 until wings 230 reach slots 232, thereby enabling toggle 226 to move distally under the action of spring 234 to the enabled and engaged ratchet state shown in FIG. 12. At this point, the toggle has rotated 180° from its reference position of the initial first state. Two cycles of moving through the first to third state take the toggle through a complete 360° rotation.

While the inventive surgical instruments and devices have been described in some detail by way of illustration, such illustration is for purposes of clarity of understanding only. It will be readily apparent to those of ordinary skill and in the art in light of the teachings herein that certain changes and modifications may be made thereto without departing from the spirit and scope of the appended claims. For example, while the multi-state ratchet mechanism described in here has typically been in the context of tools with an articulating mechanism comprising at least two links, the mechanisms may be used in an instrument comprising only a single link, a multiplicity of links, and with any number of cables or cable sets operably connecting the links. Further, while the context of the invention is considered to be surgical or medical diagnostic procedures, embodiments of the multi-sate ratchet mechanism or tools having such a mechanism may have utility in other non-medical contexts as well.

What is claimed is:

1. A surgical instrument comprising:
   a shaft having a proximal end and a distal end,
   an end effector at the distal end of the shaft,
   a movable end effector actuator at the proximal end of the shaft and operably connected to the end effector, and
   an actuator movement controller operably connectable to the end effector actuator, the actuator movement controller comprising a ratchet, a state change notifier, and a user activated state changer changeable among states in which the movement controller is:
      enabled and engaged with the end effector actuator to prevent movement of the end effector actuator in at least one of two opposite directions,
      enabled and disengaged from the end effector actuator to permit movement of the end effector actuator in a first direction and a second direction opposite to the first direction in response to continuous user input via the state changer, and
      disabled to permit movement of the end effector actuator in a first direction and a second direction opposite to the first direction in the absence of user input via the state changer,
   wherein the state changer includes a toggle linearly aligned with and operatively connected to a trigger so as to be linearly movable with the trigger and to be rotatable with respect to the trigger and
   wherein the state change notifier includes a toggle spring and a biasing ring through which the toggle movably extends, the state change notifier adapted to provide notice of an impending change in movement controller state that will be caused by further movement of the user activated state changer.

2. The surgical instrument of claim 1 wherein the movement controller, when in the state of being enabled and engaged, prevents movement of the end effector in both directions.

3. The surgical instrument of claim 1 wherein the end effector comprises jaws.

4. The surgical instrument of claim 1 wherein the toggle is operatively connected to the trigger so as to move with the trigger without rotating with respect to the trigger when the movement controller is enabled.

5. The surgical instrument of claim 4 wherein the surgical instrument further comprises a handle at the proximal end of the shaft, the trigger supported by the handle and being movable with respect to the handle, the toggle being disposed within the handle, the trigger comprising a trigger camming surface and the toggle comprising a toggle camming surface complementary to and engagable with the trigger camming surface, wherein engagement of the trigger camming surface with the toggle camming surface due to movement of the trigger creates a rotational force between the trigger and the toggle, the handle comprising a toggle guide operatively connected to the toggle to guide movement of the toggle.

6. The surgical instrument of claim 5 wherein the toggle further comprises a wing extending radially from a toggle body, the handle toggle guide comprising a slot in which the toggle wing is disposed to prevent rotation of the toggle as the toggle moves with the trigger.

7. The surgical instrument of claim 5 wherein the handle toggle guide comprises a handle camming surface complementary to and engagable with the toggle camming surface, wherein engagement of the handle camming surface with the toggle camming surface creates a rotational force between the handle and the toggle.

8. The surgical instrument of claim 5 wherein the toggle has a range of motion, and wherein the handle toggle guide is adapted to prevent rotation of the toggle in a first portion of the toggle's range of motion and to permit rotation of the toggle with respect to the trigger in a second portion of the toggle's range of motion.

9. The surgical instrument of claim 8 wherein the toggle further comprises a wing extending radially from a toggle body, the handle toggle guide comprising a slot in which the toggle wing is disposed when the toggle is in the first portion of its range of motion, the toggle wing being outside the slot when the toggle is in the second portion of its range of motion.

10. The surgical instrument of claim 1 wherein the trigger is movable from a first position in which the movement controller is enabled and engaged to a second position in which the movement controller is enabled and disengaged.

11. The surgical instrument of claim 10 wherein the trigger is movable to a third position in which the movement controller is disabled.

12. The surgical instrument of claim 11 wherein the trigger is further movable to enable and engage a disabled movement controller.

13. The surgical instrument of claim 1 wherein the state change notifier is adapted to provide tactile feedback to a user through the trigger of an impending change in movement controller state that will be caused by further movement of the trigger.

14. The surgical instrument of claim 13 wherein the tactile feedback is an increase in resistance to movement of the trigger.

15. A surgical instrument comprising:
   a shaft having a proximal end and a distal end,
   an end effector at the distal end of the shaft,
   a movable end effector actuator at the proximal end of the shaft and operably connected to the end effector, and
   an actuator movement controller operably connectable to the end effector actuator,
   the actuator movement controller comprising a state changer, a ratchet, a state change notifier, and a biasing member including a first spring, wherein the state changer includes a toggle linearly aligned with and operatively connected to a trigger so as to be linearly movable with the trigger and to be rotatable with respect to the trigger,
   the state changer being movable against the biasing member in response to a user input from a first state in which the movement controller is enabled and engaged with the end effector actuator to prevent movement of the end effector actuator in at least one of two opposite directions to a second state in which the movement controller is enabled and disengaged from the end effector actuator to permit movement of the end effector actuator in a first direction and a second direction opposite to the first direction,
   the biasing member being operably connected with the state changer to move the state changer from the second state to the first state when the user input ceases or diminishes; and wherein the state changer is movable against the biasing member in response to a user input from the second state to a third state in which the movement controller is disabled to permit movement of the end effector actuator in a first direction and a second direction opposite to the first direction in the absence of user input via the state changer and wherein the state change notifier includes a second spring and a biasing ring through which the toggle movably extends, the state change notifier adapted to provide notice of an impending change in movement controller state that will be caused by further movement of the user activated state changer.

16. The surgical instrument of claim 15 wherein the movement controller, when in the first state of being enabled and engaged, prevents movement of the end effector in both directions.

17. The surgical instrument of claim 15 wherein the end effector comprises jaws.

18. The surgical instrument of claim 15 wherein the state changer has a range of motion, the state changer being disposed with respect to the first and second springs so as to deform the first spring during a first portion of its range of motion in the second state without deforming the second spring and to deform the second spring in a second portion of its range of motion in the second state, the second spring applying a greater force on the state changer in the second portion of its range of motion than the first spring applies on the state changer in the second portion of its range of motion.

19. The surgical instrument of claim 18 wherein the second spring has a spring constant greater than a spring constant of the first spring.

20. A method of operating a medical instrument, the medical instrument comprising an end effector at the distal end of a shaft, an end effector actuator at a proximal end of the shaft, and an actuator movement controller for a ratchet, the method comprising:

actuating the end effector by moving the end effector actuator in a first direction while engaging the ratchet with the end effector actuator to prevent movement of the end effector actuator in a second direction opposite to the first direction, providing a first user input to the actuator movement controller to disengage the ratchet from the end effector actuator to permit movement of the end effector actuator in the first and second directions during the user input, wherein providing the first user input includes linearly moving a trigger and a toggle along a common axis, the toggle linearly aligned with and rotatable with respect to the trigger, the toggle extending movably through a toggle spring and biasing ring, wherein, the method further comprises providing notice that further user input will disable the actuator movement controller by moving the toggle through the toggle spring and biasing ring such that the biasing ring moves against bias provided by the toggle spring, and providing a further user input to the actuator movement controller to disable the ratchet to permit movement of the end effector actuator in the first and second directions in the absence of user input via the state changer.

21. The method of claim 20 wherein providing the first user input comprises moving the trigger a first distance and providing the further user input comprises moving the trigger to a second distance beyond the first distance.

22. The method of claim 20 wherein providing notice comprises providing a tactile sensation to a user.

23. The method of claim 22 wherein providing the first user input comprises moving the trigger a first distance, providing the further user input comprises moving the trigger to a second distance beyond the first distance, the step of providing notice comprising providing increased resistance to trigger movement after moving the trigger the first distance but prior to moving the trigger the second distance.

24. The method of claim 20 wherein, before providing the further user input, the method further comprises removing the first user input to re-engage the ratchet with the end effector actuator to prevent movement of the end effector actuator in the second direction.

25. The method of claim 24 wherein providing the first user input comprises moving a trigger and removing the first user input comprises releasing the trigger.

26. The method of claim 20 further comprising providing a subsequent user input after the further user input to re-enable the ratchet.

27. The method of claim 26 further comprising ceasing the further user input prior to providing the subsequent user input.

28. The method of claim 27 wherein providing the first user input comprises moving the trigger a first distance, providing the further user input comprises moving the trigger to a second distance beyond the first distance, ceasing the further user input comprises releasing the trigger, and providing the subsequent user input comprises moving the trigger.

\* \* \* \* \*